(12) United States Patent
Mishani et al.

(10) Patent No.: US 10,710,968 B2
(45) Date of Patent: Jul. 14, 2020

(54) RADIOLABELED ERLOTINIB ANALOGS AND USES THEREOF

(71) Applicant: Hadasit Medical Research Services and Development Ltd., Jerusalem (IL)

(72) Inventors: Eyal Yosef Mishani, Mevasseret Zion (IL); Ofer Shamni, Jerusalem (IL); Galith Rachel Abourbeh-Gofrit, Jerusalem (IL)

(73) Assignee: Hadasit Medical Research Services and Development Ltd., Jerusalem (IL)

( * ) Notice: Subject to any disclaimer, the term of this patent is extended or adjusted under 35 U.S.C. 154(b) by 0 days.

(21) Appl. No.: 16/069,546

(22) PCT Filed: Jan. 12, 2017

(86) PCT No.: PCT/IL2017/050039
§ 371 (c)(1),
(2) Date: Jul. 12, 2018

(87) PCT Pub. No.: WO2017/122205
PCT Pub. Date: Jul. 20, 2017

(65) Prior Publication Data
US 2019/0023664 A1    Jan. 24, 2019

Related U.S. Application Data

(60) Provisional application No. 62/278,029, filed on Jan. 13, 2016.

(51) Int. Cl.
| | | |
|---|---|---|
| *A61K 51/00* | (2006.01) | |
| *A61M 36/14* | (2006.01) | |
| *C07D 239/94* | (2006.01) | |
| *A61K 45/06* | (2006.01) | |
| *A61P 35/00* | (2006.01) | |
| *A61K 51/04* | (2006.01) | |
| *C07B 59/00* | (2006.01) | |
| *C12Q 1/6886* | (2018.01) | |

(52) U.S. Cl.
CPC ............ *C07D 239/94* (2013.01); *A61K 45/06* (2013.01); *A61K 51/0459* (2013.01); *A61P 35/00* (2018.01); *C07B 59/002* (2013.01); *C12Q 1/6886* (2013.01); *C07B 2200/05* (2013.01); *C12Q 2600/106* (2013.01)

(58) Field of Classification Search
CPC ............... C07D 239/94; C12Q 1/6886; C12Q 2600/106; C07B 59/002; C07B 2200/05; A61K 51/0459; A61K 45/06; A61P 35/00
USPC .......................................... 424/1.89
See application file for complete search history.

(56) References Cited

U.S. PATENT DOCUMENTS

| | | |
|---|---|---|
| 5,457,105 A | 10/1995 | Barker |
| 5,710,158 A | 1/1998 | Myers et al. |
| 5,747,498 A | 5/1998 | Schnur et al. |
| 5,760,041 A | 6/1998 | Wissner et al. |
| 5,792,771 A | 8/1998 | App et al. |
| 6,126,917 A | 10/2000 | Mishani et al. |
| 6,127,374 A | 10/2000 | Bridges |
| 6,153,617 A | 11/2000 | Bridges |
| 6,251,912 B1 | 6/2001 | Wissner et al. |
| 6,562,319 B2 | 5/2003 | Mishani et al. |
| 7,172,749 B2 | 2/2007 | Levitzki et al. |
| RE41,065 E | 12/2009 | Schnur et al. |
| 8,461,166 B2 | 6/2013 | Mishani et al. |
| 8,575,339 B2 | 11/2013 | Cheng |
| 2002/0128553 A1 | 9/2002 | Levitzki et al. |
| 2004/0242604 A1 | 12/2004 | Bhattacharya et al. |
| 2004/0265228 A1 | 12/2004 | Levitzki et al. |
| 2005/0153371 A1 | 7/2005 | Grotzfeld et al. |
| 2008/0056990 A1 | 3/2008 | Mishani et al. |
| 2008/0096881 A1 | 4/2008 | Hennequin et al. |
| 2008/0234263 A1 | 9/2008 | Hennequin et al. |
| 2013/0012528 A1 | 1/2013 | Cheng |

FOREIGN PATENT DOCUMENTS

| | | |
|---|---|---|
| CN | 103304493 | 5/2015 |
| DE | 10307165 | 9/2004 |
| EP | 0520722 | 12/1992 |
| EP | 0566226 | 11/1995 |
| EP | 0787722 | 8/1997 |
| JP | 57-144266 | 9/1982 |
| JP | 09-221478 | 8/1997 |
| WO | WO 97/30035 | 8/1997 |
| WO | WO 99/09016 | 2/1999 |
| WO | WO 00/51991 | 9/2000 |
| WO | WO 00/72849 | 12/2000 |
| WO | WO 02/073235 | 9/2002 |
| WO | WO 03/068264 | 8/2003 |
| WO | WO 2004/046101 | 6/2004 |

(Continued)

OTHER PUBLICATIONS

Zhang et al. Curr. Top. Med. Chem. 2007, 7, 1817-1828.*

(Continued)

*Primary Examiner* — Michael G. Hartley
*Assistant Examiner* — Sean R Donohue

(57) ABSTRACT

Radiolabeled compounds which are erlotinib analogs that feature a radioactive halogen and processes of preparing same are disclosed. Uses of these radiolabeled compounds in radioimaging, for identifying and monitoring a level, distribution and/or mutational status of deregulated EGFR, and/or in radiotherapy, are also disclosed.

27 Claims, 5 Drawing Sheets
(4 of 5 Drawing Sheet(s) Filed in Color)

(56) References Cited

FOREIGN PATENT DOCUMENTS

| WO | WO 2004/064718 | 8/2004 |
|---|---|---|
| WO | WO 2005/023315 | 3/2005 |
| WO | WO 2005/026156 | 3/2005 |
| WO | WO 2005/028469 | 3/2005 |
| WO | WO 04/064718 | 8/2005 |
| WO | WO 2007/029251 | 3/2007 |
| WO | WO 2010/013139 | 2/2010 |
| WO | WO 2014/118197 | 8/2014 |
| WO | WO 2017/122205 | 7/2017 |

OTHER PUBLICATIONS

Ferrieri Handbook Radiopharm.: Radiochem. Appl. 2003, 229-282.*
Supplementary European Search Report and the European Search Opinion dated Jun. 3, 2019 From the European Patent Office Re. Application No. 17738289.2. (8 pages).
Chen et al. "Synthesis and Evaluation of Novel F-18 Labeled 4-Aminoquinazoline Derivatives: Potential PET Imaging Agents for Tumor Detection", Bioorganic & Medicinal Chemistry Letters. XP028504438, 22(14): 4745-4749, Available Online May 24, 2012.
Communication Pursuant to Article 94(3) EPC dated Dec. 20, 2007 From the European Patent Office Re. Application No. 00930818.0.
International Preliminary Report on Patentability dated Mar. 20, 2008 From the International Bureau of WIPO Re. Application No. PCT/IL2006/001038.
Communication Pursuant to Article 94(3) EPC dated Jan. 4, 2012 From the European Patent Office Re. Application No. 06780468.2.
Communication Pursuant to Article 94(3) EPC dated Jun. 15, 2009 From the European Patent Office Re. Application No. 06780468.2.
Communication Pursuant to Article 94(3) EPC dated Oct. 15, 2010 From the European Patent Office Re. Application No. 06780468.2.
Communication Pursuant to Article 94(3) EPC dated Feb. 21, 2013 From the European Patent Office Re. Application No. 06780468.2.
Communication Pursuant to Article 94(3) EPC dated Jan. 24, 2014 From the European Patent Office Re. Application No. 06780468.2.
Communication Pursuant to Rules 109 and 110 EPC dated Apr. 28, 2006 From the European Patent Office Re. Application No. 04770505.8.
European Search Report Under Rule 112 EPC dated Jul. 24, 2007 From the European Patent Office Re. Application No. 04770505.8.
International Preliminary Report on Patentability dated Mar. 23, 2006 From the International Bureau of WIPO Re. Application No. PCT/IL2004/000834.
International Preliminary Report on Patentability dated Jul. 26, 2018 From the International Bureau of WIPO Re. Application No. PCT/IL2017/050039. (7 pages).
International Search Report and the Written Opinion dated Apr. 6, 2017 From the International Searching Authority Re. Application No. PCT/IL2017/050039. (11 pages).
International Search Report and the Written Opinion dated Feb. 12, 2007 From the International Searching Authority Re. Application No. PCT/IL2006/001038.
Office Action dated Apr. 6, 2009 From the Israeli Patent Office Re. Application No. 174237 and Its Translation Into English.
Office Action dated Mar. 15, 2010 From the Israeli Patent Office Re. Application No. 157812 and Its Translation Into English.
Office Action dated Jun. 29, 2008 From the Israeli Patent Office Re. Application No. 157812.
Official Action dated Jul. 22, 2005 From the U.S. Appl. No. 10/659,747.
Official Action dated Apr. 24, 2012 From the U.S. Appl. No. 11/714,760.
Requisition by the Examiner dated Mar. 5, 2009 From the Canadian Intellectual Property Office Re. Application No. 2,440,552.
Restriction Official Action dated Aug. 4, 2011 From the U.S. Appl. No. 11/714,760.
Restriction Official Action dated Nov. 7, 2011 From the U.S. Appl. No. 11/714,760.
Restriction Official Action dated Dec. 13, 2011 From the U.S. Appl. No. 11/714,760.
Supplementary European Search Report dated Jul. 4, 2007 From the European Patent Office Re. Application No. 02702703.6.
Translation of Official Action dated Sep. 9, 2008 From the Japanese Patent Office Re. Application No. 2002-572442.
Abourbeh et al. "Identifying Erlotinib-Sensitive Non-Small Cell Lung Carcinoma Tumors in Mice Using [11C]Erlotinib PET", EJNMMI Research, 5(4): 1-10, Feb. 12, 2015.
Artega "The Epidermal Growth Factor: From Mutant Oncogene in Nonhuman Cancers to Therapeutic Target in Human Neoplasia", Journal of Clinical Oncology, 19(18): 32s-40s, 2001.
Bahce et al. "Development of [11C]Erlotinib Positron emission Tomography for In Vivo Evaluation of EGF Receptor Mutational Status", Clinical Cancer Research, 19(1): 183-193, Published Online Nov. 7, 2012.
Baselga et al. "ZD1839 ('Iressa') 1,2 as an Anticancer Agent", Drugs, 60(Suppl.1): 33-40, 2000.
Ben-David et al. "Radiosynthesis of ML03, A Novel Positron Emission Tomography Biomarker for Targeting Epidermal Growth Factor Receptor Via the Labeling Synthon: [11C] Acryloyl Chloride", Applied Radiation and Isotopes, 58: 209-217, 2003.
Bonasera et al. "Potential 18F-Labeled Biomarkers for Epidermal Growth Factor Receptor Tyrosine Kinase", Nuclear Medicine and Biology, 28: 359-374, 2001.
Bridges et al. "Tryrosine Kinase Inhibitors. 8. An Unusually Steep Structure-Activity Relationship for Analogues of 4-(3-Bromoanilinio)-6, 7-Dimethoxyquinazoline (PD 153035, A Potent Inhibitor of the Epidermal Growth Factor Receptor", Journal of Medical Chemistry, 39: 267-276, 1996.
Dissoki et al. "Modified PEG-Anilinoquinazoline Derivatives as Potential EGFR PET Agents", Journal of labelled Compounds and Radiopharmaceuticals, 12 P., Oct. 29, 2008.
Faaland et al. "Rapid Uptake of Tyrphostin into A431 Human Epidermoid Cells is Followed by Delayed Inhibition of Epidermal Growth Factor (EGF)-Stimulated EGF Receptor Tyrosine Kinase Activity", Molecular and Cellular Biology, 11 (5): 2697-2703, May 1991.
Fry et al. "Specific Irreversible Inactivation of the Epidermal Growth Factor Receptor and ErbB2 by A New Tyrosine Kinase Inhibitor", Proc. Natl. Acad. Sci. USA, 95: 12022-12027, 1998.
Gazit et al. "Tyrphostins IV—Highly Potent inhibitors of EGF Receptor Kinase. Stricture—Activity Relationship Study of 4-Anilidoquinazolines", Bioorganic & Medical Chemistry, 4 (8): 1203-1207, 1996.
Han et al. "Tyrphostin AG 1478 Preferentially Inhibits Human Glioma Cells Expressing Truncated Rather Than Wild-Type Epidermal Growth Factor Receptors". Abstract.
Johnstrom et al. "Synthesis of [Methoxy-11C]PD153035, A Selective EGF Receptor Tyrosine Kinase Inhibitor", Journal of Labbelled Compounds and Radiogharmaceuticals, XLI: 623-629, 1998. p. 627, Fig.3.
Levitzki et al. "Tyrosin Kinase Inhibition: an Approach to Drug Development", Science, 267: 1782-1788, 1995.
Lowry et al. "Mechanism and Theory in Organic Chemistry": 633, 1987.
Memon et al. "Positron Emission Tomography (PET) Imaging With [11C]-Labeled Erlotinib: A Micro-PET Study on Mice With Lung Tumor Xenografts", Cancer Research, 69(3): 873-878, Published Online Jan. 20, 2009.
Mishani et al. "[C-11] Acryloyl Chloride—A Fully Automated Preparation and Reaction With Model Amine", Journal of Labelled Compound and Radiopharmacology, 44(Suppl.1): S475-S476, 2001. Abstract.
Mishani et al. "Carbon-11 Labeled Irreversible Inhibitors for Mapping Epidermal Growth Factor Receptor Tyrosine Kinase (EGFR-TK)", Journal of Labelled Compounds and Radiopharmaceuticals, 44(Suppl.1): S99-S101, 2001.
Mishani et al. "Carbon-11 Labeling of -Dimethylamino-But-2-Enoic Acid [4-(Phenylamino)-Quinazolin-6-Y1]-Amides, A New

(56) References Cited

OTHER PUBLICATIONS

Class of EGFR Irreversible Inhibitors", Journal of Labelled Compounds and Radiopharmaceuticals, 46(S1): S2, 2003. Abstract.
Mishani et al. "Novel Carbon-11 Labeled 4-Dimethylamino-But-2-Enoic Acid [4-(Phenylamino)-Quinazoline-6-Yl]-Amides: Potential PET Bioprobes for Molecular Imaging of EGFR-Positive Tumors", Nuclear Medicine and Biology, 31(4): 469-476, 2004.
Mishani et al. "Novel Carbon-11 Labeled 4-Dimethylamino-But-2-Enoic Acid [4-(Phenylamino)-Quinazoline-6-Yl]-Amides: Potential PET Bioprobes for Molecular Imaging of EGFR-Positive Tumors", Nuclear Medicine and Biology, 31(4): 469-476, 2004. p. 474, col. 2, § 4-p. 475, Figs.2, 3.
Miyaji et al. "Effect of Tyrophostin on Cell Growth and Tyrosine Kinase Activity of Epidermal Growth Factor Receptor in Human Gliomas", Journal of Neurosurgery, 81: 411-419, 1994.
Nelson et al. "Cytoskeletal and Morphological Changes Associated With the Specific Suppression of the Epidermal Growth Factor Receptor Tyrosine Kinase Activity in A431 Human Epidermoid Carcinoma", Experimental Cell Research, 233: 383-390, 1997.
Ortu et al. "Labeled EGFR-TK Irreversible Inhibitor (ML03) In Vitro and In Vivo Properties, Potential as PET Biomarker for Cancer and Feasibility as Anticancer Drug", International Journal of Cancer, 101: 360-370, 2002. Conclusion, p. 361, col. 1, § 1, Fig.1.
Paez et al. "EGFR Mutations in Lung Cancer: Correlation With Clinical Response to Gefitinib Therapy", Science, 304: 1497-1500, 2004.
Pal et al. "Molecular Imaging of EGFR Kinase Activity in Tumors With 124I-Labeled Small Molecular Tracer and Positron Emission Tomography", Molecular Imaging and Biology, 8(5): 262-277, Sep. 2006.
Pal et al. "Radiosynthesis and Initial In Vitro Evaluation of [18F]-PEG6-IPQA-A Novel PET Radiotracer for Imaging EGFR Expression-Activity in Lung Carcinomas", Molecular imaging and Biology, 13(5): 853-861, Oct. 2011.
Park et al. "Erlotinib Binds Both inactive and Active Conformations of the EGFR Tyrosine Kinase Domain", The Biochemical Journal, 448(3): 417-423, Dec. 15, 2012.
Roberts et al. Basic Principals of Organic Chemistry: 800-802, 1964.
Ryan Petrulli et al. "Quantitative Analysis of [11C]-Erlotinib PET Demonstrates Specific Binding for Activating Mutations of the EGFR Kinase Domain", Neoplasia, 15(12): 1347-1353, Dec. 2013.

Shaul et al. "Novel Iodine-124 Labeled EGFR Inhibitors as Potential PET Agents for Molecular Imaging in Cancer", Bioorganic & Medicinal Cyhemistry, 12: 3421-3429, 2004. p. 3422, col. 1, Figs.2, 4.
Singh et al. "Inhibitors of the Epidermal Growth Factor Receptor Protein Tyrosine Kinase: A Quantitative Structure-Activity Relationship Analysis", J. Enzyme Inhibitation, 13: 125-134, 1998. Esp. compounds 7-56 in Table 1 p. 126-127. Claims X: 1-3, 6, 8-11, 22/Y: 4, 5 , 7.
Smaill et al. "Tyrosine Kinase Inhibitors. 15. 4-(Phenylamino)Quiazoline and 4-(Phenylamino)Pyrido[d]Pyrimidine Acrylamides as Irreversible Inhibitors of the ATP Binding Site of the Epidermal Growth Factor Receptor", Journal of Medicinal Chemistry, 42(10): 1802-1815, 1999. Tables 1, 2, Scheme 1, 2, Abstract.
Smaill et al. "Tyrosine Kinase Inhibitors. 15. 4-(Phenylamino)Quinazoline and 4-(Phenylamino)Pyrido[D]Pyrimidine Acrylamides as Irreversible Inhibitors of the ATP Binding Site of the Epidermal Growth Factor Receptor", Journal of Medicinal Chemistry, 42 (10): 1803-1815. 1999.
Smaill et al. "Tyrosine Kinase Inhibitors. 17. Irreversible Inhibitors of the Epidermal Growth Factor Receptor: 4-(Phenylamino)Quinazoline- and 4-(Phenylamino)Pyrido[3,2-d]Pyrimidine-6-Acrylamides Bearing Additional Solubilizing Functions", Journal of Medicinal Chemistry, 43(7): 1380-1397, 2000. Compound 18, 25-27, Table 1.
Smaill et al. "Tyrosine Kinase Inhibitors. 17. Irreversible Inhibitors of the Epidermal Growth Factor Receptor: 4-(Phenylamino)Quinazoline- and 4-(Phenylamino)Pyrido[3,2-D]Pyrimidine-6-Acrylamides Bearing Additional Solubilizing Functions", Journal of Medicinal Chemistry, 43: 1380-1397, 2000. Table 1, Compound 19.
Stamos et al. "Structure of the Epidermal Growth Factor Receptor Kinase Domain Alone and in Complex With a 4-Anilinoquinazoline Inhibitor", The Journal of Biological Chemistry, 277(48): 46265-46272, Published Online Aug. 23, 2002.
Tsou et al. "6-Substituted-4-(3-Bromophenylamino)Quinazolines as Putative Irreversible Inhibitors of the Epidermal Growth Factor Receptor (EGFR) and Human Epidermal Growth Factor Receptor (HER-2) Tyrosine Kinases With Enhanced Antitumor Activity", Journal of Medicinal Chemistry, 44(17): 2719-2734, 2001.
Weber et al. "Erlotinib Accumulation in Brain Metastases From Non-Small Cell Lung Cancer: Visualization by Positron Emission Tomography in a Patient Harboring a Mutation in the Epidermal Growth Factor Receptor", Journal of Thoracic Oncology, 6(7): 1287-1289, Jul. 2011.

\* cited by examiner

RADIOLABELED ERLOTINIB ANALOGS AND USES THEREOF

RELATED APPLICATIONS

This application is a National Phase of PCT Patent Application No. PCT/IL2017/050039 having International filing date of Jan. 12, 2017, which claims the benefit of priority under 35 USC § 119(e) of U.S. Provisional Patent Application No. 62/278,029 filed on Jan. 13, 2016. The contents of the above applications are all incorporated by reference as if fully set forth herein in their entirety.

FIELD AND BACKGROUND OF THE INVENTION

The present invention, in some embodiments thereof, relates to radiopharmaceuticals and, more particularly, but not exclusively, to novel radiolabeled EGFR-TK inhibitors and their use in radioimaging (e.g., PET or SPECT) and in radiotherapy.

Polypeptides such as growth factors, differentiation factors, and hormones often mediate their pleiotropic actions by binding to and activating cell surface receptors with an intrinsic intracellular protein tyrosine kinase activity. The epidermal growth factor receptor (EGFR) is one such receptor.

Receptor tyrosine kinases are large enzymes which span the cell membrane and possess an extracellular binding domain for growth factors such as the epidermal growth factor, a transmembrane domain, and an intracellular portion which functions as a kinase to phosphorylate specific tyrosine residues in proteins and hence to influence cell proliferation. It is known that such kinases are frequently aberrantly expressed in common human cancers. It has also been shown that the epidermal growth factor receptor (EGFR) is mutated and/or overexpressed in many human cancers such as brain, lung, squamous cell, bladder, gastric, breast, head and neck, oesophageal, gynecological and thyroid tumors.

Some mutation variants in the tyrosine kinase domain of the EGFR gene result in increased activity of the tyrosine kinase and in constitutive activity of the receptor, resulting in uncontrolled cell proliferation. Such mutation variants are commonly termed "activating mutations", and are observed, for example, in patients having non-small cells lung cancer (NSCLC). Activating mutations in the tyrosine kinase domain of the EGFR gene typically confer sensitivity to EGFR tyrosine kinase small molecule inhibitors, whereby other mutation variants in the EGFR may result in insensitivity or resistance to EGFR-TK small molecule inhibitors.

EGFR small molecule tyrosine kinase inhibitors (abbreviated as EGFR-TKIs or simply as TKIs) bind to the tyrosine kinase domain of the EGFR on the cytoplasmic side of the receptor, and inhibit its tyrosine kinase activity. Without kinase activity, the EGFR is unable to further bind to and activate downstream proteins. By interfering with (halting) the signaling cascade in cells that rely on this pathway for growth, cell proliferation, survival and migration are diminished. EGFR-TKIs are therefore considered a selected therapy in the presence of activating mutation in the tyrosine kinase domain of the EGFR gene, as, for example, in some cases of NSCLC.

When aberrant cell proliferation is associated with deregulated expression and/or activity of EGFR that does not result from an activating mutation in the tyrosine kinase domain of the EGFR gene, the treatment regime typically utilizes, for example, compounds which inhibit DNA synthesis. Such compounds are known as cytotoxic agents, and are disadvantageously characterized by adverse side effects due to their non-selectivity.

Erlotinib, also known as Tarceva™, or N-(3-ethynylphenyl)-6,7-bis(2-methoxyethoxy)quinazolin-4-amine, is a reversible EGFR-TKI, featuring the following chemical structure:

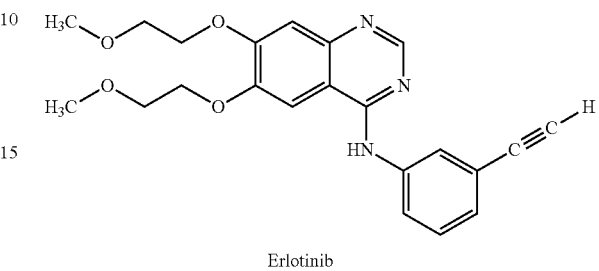

Erlotinib

Erlotinib is described, for example, in U.S. Pat. Nos. 5,747,498 and RE41065, which are incorporated by reference as if fully set forth herein.

Erlotinib has a 4-anilinoquinazoline skeleton, and features an ethynyl substituent on the aniline ring and methoxyethoxy (Methoxy-terminated ethylene glycol) substituents at positions 6 and 7 of the quinazoline ring.

Currently, erlotinib is approved for the treatment of NSCLC and pancreatic cancer.

Lung cancer accounts for almost 30% of cancer-related deaths, with non-small cell lung cancer (NSCLC) representing approximately 80% of lung cancer cases.

There are currently various first-line therapeutic approaches for patients with advanced NSCLC. Since overexpression of the epidermal growth factor receptor (EGFR) has been detected in the majority of NSCLC tumors, this tyrosine kinase (TK) receptor emerged as the focus of various targeted therapeutic approaches. EGFR-TK selective small molecule inhibitors (EGFR-TKIs), such as gefitinib and erlotinib, gained FDA approval approximately 12 years ago, for treating advanced NSCLC.

It has been recognized that a successful treatment of NSCLC is largely determined by the histopathological and molecular characteristics of the tumors. Clinical experience has taught that only patients whose tumors harbor activating mutations in the TK domain of the EGFR gene, such as the del(E746-A750) and the L858R mutations, benefit from TKI-therapy over cytotoxic chemotherapy. Therefore, at present, first-line treatment of NSCLC patients using EGFR-TKIs is recommended only for patients whose tumors harbor such activating mutations [Carnio et al. *Semin Oncol* 2014, 41:69-92; Dillon et al. *Lancet Oncol* 2012, 13:764-765].

Activating mutations in the TK domain of the EGFR gene occur in 10-30% of NSCLC patients [Ratti M. and Tomasello G. *Anticancer Drugs* 2014, 25:127-139], and evidence of their presence is a prerequisite for the initiation of first-line targeted therapy with selective EGFR-TKIs, such as erlotinib.

At present, the identification and selection of NSCLC patients who are candidates for first line treatment with selective EGFR-TKIs require biopsy of the primary tumor and further analysis by genotyping and/or immunohistochemistry (IHC) of tissue specimens for verifying the mutational status of the EGFR. Various techniques of obtaining lung biopsies exist, which are invasive and costly, necessitate tissue samples of sufficient quality, and require time for mutation analysis. Moreover, the histopathological and molecular characteristics of tissue specimens retrieved from the primary tumor do not necessarily represent those of distant metastases, nor do they provide information about their presence and location.

Furthermore, the majority of TKI-treated NSCLC patients ultimately develop resistance to treatment, with the most common mechanism of resistance involving the emergence of the secondary gate-keeper T790M mutation in exon 20 of the EGFR gene [Riely et al. Clin Cancer Res 2007, 13:5150-5155; Yu et al. Clin Cancer Res 2013, 19:2240-2247]. Thus, monitoring response to treatment during TKI-therapy is essential, since adjustments and modifications of the treatment approach throughout the course of treatment may be required. However, similarly to the process of patient selection prior to treatment with TKIs, identification of patients whose tumors harbor the secondary T790M mutation typically requires interfering procedures such as biopsy. Tumor biopsies, however, are less applicable for longitudinal monitoring of the EGFR's mutational status during the course of treatment. Thus, the prevailing approach of patient selection is not optimal for obtaining longitudinal information about the molecular characteristics of EGFR in tumors.

The use of radioactive nuclides for medicinal purposes is well known in the art. Biologically active compounds that bind to specific cell surface receptors or modify cellular functions have received some consideration as radiopharmaceuticals, and therefore, when labeled with a radioactive nuclide, such compounds are used as biospecific agents in radioimaging and/or radiotherapy.

Positron emission tomography (PET), a nuclear imaging technique which allows the three-dimensional, quantitative determination of the distribution of radioactivity within the human body, is widely recognized as an important tool for the measurement of physiological, biochemical, and pharmacological function at a molecular level, both in healthy and pathological states. PET involves the administration of a molecule labeled with a positron-emitting nuclide (radiotracer) such as $^{15}$O, $^{13}$N, $^{11}$C and $^{18}$F, which have half-lives of 2, 10, 20, and 110 minutes, respectively.

Similarly, single photon emission computed tomography (SPECT) is a form of nuclear imaging, in which emissions from radioactive compounds, labeled with gamma-emitting radionuclides, are used to create 3D images of radioactivity distribution in vivo. SPECT requires the administration of a molecule labeled with a gamma-emitting nuclide, such as $^{99m}$Tc, $^{67}$Ga, $^{111}$In and $^{123}$I.

Radiotracers that bind to EGFR-TK and thereby allow, through a nuclear imaging technique, such as PET, mapping and quantification of this receptor-kinase, and detecting changes in its levels of expression, and optionally, depending on the radiotracer used, can be utilized also in radiotherapy, have been disclosed, for example, in U.S. Pat. Nos. 6,126,917, 6,562,319, 7,172,749, and 8,461,166.

Non-invasive molecular imaging techniques such as positron emission tomography (PET) have been suggested for identifying EGFR's mutational status in tumors in order to determine if patients are expected to be responsive to TKI-therapy, prior to treatment, and to monitor the EGFR's mutational status during the course of treatment. A use of [$^{11}$C]erlotinib PET for identifying NSCLC tumors that harbor exon-19 in-frame deletions in human subjects and in mouse models, has been described in Bahce et al. Clin Cancer Res 2012, 19:183-193; and Weber et al. J Thorac Oncol 2011, 6:1287-1289, for human subjects, and in Memon et al. Cancer Res 2009, 69:873-878; and Petrulli et al. Neoplasia 2013, 15:1347-1353, for mice models.

Recently, the ability to differentiate erlotinib-responsive NSCLC tumors in mice from non-responsive or resistant tumors, using [$^{11}$C]erlotinib PET, has been reported. See, Abourbeh et al. EJNMMI Res 2015, 5:4.

Additional background art includes U.S. Pat. No. 8,575,339, which describes, inter alia, halo (e.g., fluoro)-containing derivatives of erlotinib; and PCT International Patent Application Publication No. WO 2014/118197, which describes fluorine-18 radiolabeled afatinib analogs for nuclear imaging of EGFR and for determining the mutational status of EGFR.

SUMMARY OF THE INVENTION

A need exists for improved non-invasive molecular imaging methodologies capable of identifying diseases and disorders that are associated with deregulated expression and/or activity of EGFR-TK, such as NSCLC tumors, and are responsive to treatment with reversible EGFR-TK inhibitors (EGFR-TKIs). Such methodologies can facilitate selection of patients prior to EGFR-TKI treatment, and further enable longitudinal monitoring of the EGFR's mutational status during therapy.

The present inventors have now designed and practiced novel radiolabeled compounds derived from erlotinib, which may be efficiently employed in non-invasive radioimaging methodologies for identifying diseases and disorders associated with deregulated expression and/or activity of EGFR-TK, which are responsive to treatment with EGFR-TKIs, and for monitoring EGFR's mutational status before and/or during treatment.

These radiolabeled compounds can be readily prepared via one-step or two-step radiosynthesis, and are characterized by minimal and even nullified interference with the affinity to EGFR.

According to an aspect of some embodiments of the present invention there is provided a radiolabeled compound represented by general Formula Ia or Ib:

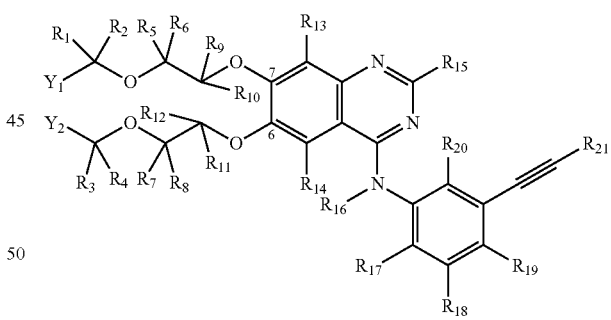

Formula Ia

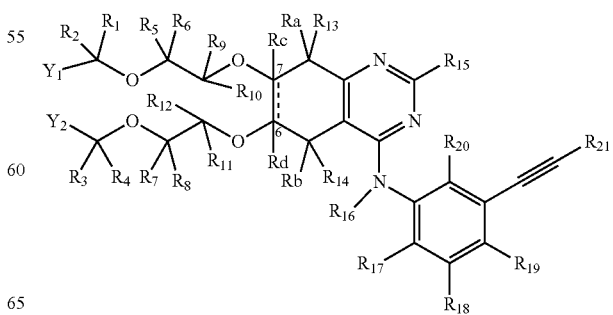

Formula Ib wherein:

the dashed line in Formula Ia represents an optional unsaturated bond;

$R_1$-$R_{21}$, Ra and Rb are each independently selected from the group consisting of hydrogen, alkyl, cycloalkyl, aryl, heteroalicyclic, heteroaryl, alkoxy, aryloxy, thioalkoxy, thioaryloxy, hydroxyl, halogen, trihaloalkyl, trihaloalkoxy, amine, cyano, nitro, carbonyl, thiocarbonyl, carboxylate, thioacarboxylate, amide, thioamide, carbamate, thiocarbamate, alkaryl, aralkyl, sulfinyl, sylfonyl, sulfonate, and sulfonamide;

Rc and Rd are each absent, in case the dashed line is an unsaturated (double) bond, or, in case the dashed line is absent, are each independently selected from the group consisting of hydrogen, alkyl, cycloalkyl, aryl, heteroalicyclic, heteroaryl, alkoxy, aryloxy, thioalkoxy, thioaryloxy, hydroxyl, halogen, trihaloalkyl, trihaloalkoxy, amine, cyano, nitro, carbonyl, thiocarbonyl, carboxylate, thioacarboxylate, amide, thioamide, carbamate, thiocarbamate, alkaryl, aralkyl, sulfinyl, sylfonyl, sulfonate, and sulfonamide; and $Y_1$ and $Y_2$ are each independently selected from hydrogen, alkyl, alkenyl, alkynyl, cycloalkyl, aryl, heteroalicyclic, heteroaryl, alkoxy, aryloxy, thioalkoxy, thioaryloxy, hydroxyl, halogen, trihaloalkyl, trihaloalkoxy, amine, cyano, nitro, carbonyl, thiocarbonyl, carboxylate, thioacarboxylate, amide, thioamide, carbamate, thiocarbamate, alkaryl, aralkyl, sulfinyl, sylfonyl, sulfonate, sulfonamide, a substituted or unsubstituted, saturated or unsaturated hydrocarbon chain of 1 to 20 carbon atoms, optionally interrupted by one or more heteroatoms, a radioactive halogen, and Q, wherein Q is a chemical moiety comprising a radioactive halogen, provided that at least one of $Y_1$ and $Y_2$ is or comprises a radioactive halogen.

According to some of any of the embodiments described herein, at least one of $Y_1$ and $Y_2$ is the Q.

According to some of any of the embodiments described herein, Q is a saturated or unsaturated hydrocarbon chain of 2 to 20 carbon atoms, optionally interrupted by one or more heteroatoms, substituted by or terminating with the radioactive halogen, and optionally substituted by one or more additional substituents.

According to some of any of the embodiments described herein, Q is an alkylene chain or is or comprises an alkylene glycol or a derivative thereof, each being substituted by or terminating with the radioactive halogen.

According to some of any of the embodiments described herein, Q is represented by (CR'R")nX, wherein R' and R" are each independently selected from hydrogen, alkyl, cycloalkyl, aryl, heteroalicyclic, heteroaryl, alkoxy, aryloxy, thioalkoxy, thioaryloxy, hydroxyl, halogen, trihaloalkyl, trihaloalkoxy, amine, cyano, nitro, carbonyl, thiocarbonyl, carboxylate, thioacarboxylate, amide, thioamide, carbamate, thiocarbamate, alkaryl, aralkyl, sulfinyl, sylfonyl, sulfonate, and sulfonamide;

n is an integer of from 1 to 20; and

X is the radioactive halogen.

According to some of any of the embodiments described herein, each of R' and R" is hydrogen.

According to some of any of the embodiments described herein, n is an integer ranging from 1 to 10, or from 1 to 6, or from 1 to 4.

According to some of any of the embodiments described herein, n is 2.

According to some of any of the embodiments described herein, at least one of $Y_1$ and $Y_2$ is the radioactive halogen.

According to some of any of the embodiments described herein, each of $R_1$-$R_4$ is hydrogen.

According to some of any of the embodiments described herein, each of $R_5$-$R_{12}$ is hydrogen.

According to some of any of the embodiments described herein, each of $R_{17}$-$R_{21}$ is hydrogen.

According to some of any of the embodiments described herein, the radiolabeled compound is represented by Formula Ia.

According to some of any of the embodiments described herein, each of $R_{13}$-$R_{16}$ is hydrogen.

According to some of any of the embodiments described herein, the radiolabeled compound is represented by Formula Ib.

According to some of any of the embodiments described herein, each of Ra, Rb, Rc (if present), Rd (if present) and $R_{13}$-$R_{16}$ is hydrogen.

According to some of any of the embodiments described herein, the radioactive halogen is fluorine-18.

According to some of any of the embodiments described herein, the radioactive halogen is a radioactive bromine.

According to some of any of the embodiments described herein, the radioactive halogen is a radioactive iodine.

According to an aspect of some embodiments of the present invention there is provided a pharmaceutical composition comprising as an active ingredient the radiolabeled compound according to any one of the respective embodiments and any combination thereof and a pharmaceutical acceptable carrier.

According to an aspect of some embodiments of the present invention there is provided a radiolabeled compound or a composition comprising same according to any one of the respective embodiments and any combination thereof, for use in radioimaging.

According to some of any of the embodiments described herein, the radioimaging comprises administering to the patient the radiolabeled compound or the composition and employing a nuclear imaging technique to thereby determine a level and/or distribution of the compound in the patient's body or a portion thereof.

According to some of any of the embodiments described herein, the radioimaging is for monitoring or determining a level and/or distribution and/or mutational status of an epidermal growth factor receptor (EGFR) within the body of the patient.

According to some of any of the embodiments described herein, the radioimaging is for determining if the patient has a disease or disorder associated with deregulated expression and/or activity of EGFR.

According to some of any of the embodiments described herein, the disease or disorder is a proliferative disease or disorder.

According to some of any of the embodiments described herein, the radioimaging is for monitoring or determining a presence or absence of an activating mutation in the tyrosine kinase domain of an EGFR gene which confers sensitivity to an inhibitor of EGFR-TK.

According to some of any of the embodiments described herein, the radioimaging is for determining if the patient has a disease or disorder treatable by an inhibitor of EGFR-TK.

According to some of any of the embodiments described herein, the radioimaging is for determining if the patient is responsive to a treatment with an inhibitor of EGFR-TK inhibitor.

According to some of any of the embodiments described herein, the inhibitor of EGFR-TK is erlotinib.

According to some of any of the embodiments described herein, the radioimaging is for determining if a patient is responsive to a treatment with an inhibitor of EGFR-TK.

According to some of any of the embodiments described herein, the patient is diagnosed as having, or as suspected of having, a disease or disorder associated with deregulated expression and/or activity of EGFR.

According to some of any of the embodiments described herein, the patient is diagnosed as having, or as suspected of having, a proliferative disease or disorder.

According to some of any of the embodiments described herein, the proliferative disease or disorder is selected from the group consisting of non-small cell lung cancer (NSCLC), pancreatic cancer, head and neck squamous cell carcinoma (HNSCC), brain cancer, breast cancer, esophageal cancer, gastric cancer, renal cancer, cervical cancer, ovarian cancer, hepatocellular cancer, malignant glioma, prostate cancer, colorectal cancer (CRC), bladder cancer, gynecological cancer, thyroid cancer and lymphoma.

According to some of any of the embodiments described herein, the patient is diagnosed as having, or as suspected of having, NSCLC.

According to some of any of the embodiments described herein, the radioimaging is performed following the treatment, and is for determining an emergence of a resistance to the treatment.

According to some of any of the embodiments described herein, the inhibitor of EGFR-TK is erlotinib.

According to some of any of the embodiments described herein, the radioimaging is for determining a mutational status of EGFR in a patient.

According to an aspect of some embodiments of the present invention there is provided a radiolabeled compound or a composition comprising same according to any one of the respective embodiments and any combination thereof, for use in the treatment of a patient diagnosed with a disease or disorder associated with deregulated expression and/or activity of EGFR, the treatment comprising:

administering the radiolabeled compound or the composition to the patient;

determining a level and/or distribution of the radiolabeled compound in the patient's body or a portion thereof by employing a nuclear imaging technique, the level and/or distribution being indicative of the patient's responsiveness to a treatment with an inhibitor of EGFR-TK; and based on the determining, administering to the patient an inhibitor of EGFR-TK or an agent for regulating the expression and/or activity of EGFR other than an inhibitor of EGFR-TK.

According to some of any of the embodiments described herein, following the determining the patient is administered with the inhibitor of EGFR-TK for a first time period, the method further comprising, following the first time period, determining an emergence of a resistance to the inhibitor of EGFR-TK, the determining comprising:

administering the radiolabeled compound or the composition to the patient;

determining a level and/or distribution of the radiolabeled compound in the patient's body or the portion thereof by employing the nuclear imaging technique, the level and/or distribution being indicative of the patient's responsiveness to a treatment of an inhibitor of EGFR-TK; and based on the determining, administering to the patient the inhibitor of EGFR-TK for a second time period or administering to the patient the other agent for regulating the expression and/or activity of EGFR for the second time period.

According to some of any of the embodiments described herein, the technique is positron emission tomography.

According to some of any of the embodiments described herein, the technique is single photon emission computed tomography.

According to an aspect of some embodiments of the present invention there is provided a radiolabeled compound or a composition comprising same according to any one of the respective embodiments and any combination thereof, for use in radiotherapy in a patient in need thereof.

According to some of any of the embodiments described herein, the patient is diagnosed with deregulated expression and/or activity of EGFR.

According to some of any of the embodiments described herein, the patient is diagnosed with a proliferative disease or disorder.

According to some of any of the embodiments described herein, the patient is diagnosed as having an activating mutation in the tyrosine kinase domain of EGFR gene which confers sensitivity to an inhibitor of EGFR-TK.

According to some of any of the embodiments described herein, patient is diagnosed as having a disease or disorder that is treatable by an inhibitor of EGFR-TK.

According to an aspect of some embodiments of the present invention there is provided a process of preparing a radiolabeled compound according to any one of the respective embodiments and any combination thereof, the process comprising reacting a compound represented by Formula IIa or IIb:

Formula IIa

Formula IIb wherein:

$A_1$ is $-CR_1R_2B_1$, $-CR_1R_2Q_1W_1$, or forms with the oxygen to which it is attached $W_1$;

$A_2$ is $-CR_3R_4B_2$, $-CR_3R_4Q_2W_2$, or forms with the oxygen to which it attached $W_1$;

$B_1$ and $B_2$ are each independently as defined for $R_1$-$R_{21}$;

$Q_1$ and $Q_2$ are each independently as defined for Q or is absent;

$W_1$ and $W_2$ are each independently a reactive group; and all other variables are as defined for Formula Ia or Ib, provided that at least one of $A_1$ and $A_2$ forms with the oxygen to which it is attached, or comprises, the reactive group, with a compound represented by Formula III(1) and/or III(2):

    Formula III(1)

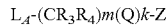    Formula III(2)

wherein:

$L_4$ is a leaving group;

Z is the radioactive halogen;

m is 0 or 1; and k is 0 or 1, whereas:

the compound of Formula III(1) is reacted with a compound represented by Formula IIa or IIb in which $A_1$ forms, or comprises, the $W_1$, and a compound represented by Formula III(2) is reacted with a compound represented by Formula IIa or IIb in which $A_2$ forms a part of, or comprises, the $W_2$;

when $A_1$ forms with the oxygen atom to which it is attached the $W_1$, m in Formula III(1) is 1;

when $A_2$ forms with the oxygen atom to which it is attached the $W_2$, m in Formula III(2) is 1;

when $A_1$ is —$CR_1R_2Q_1W_1$, m and k in Formula III(1) are each 0; and when $A_2$ is —$CR_3R_4Q_2W_2$, m and k in Formula III(2) are each 0.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
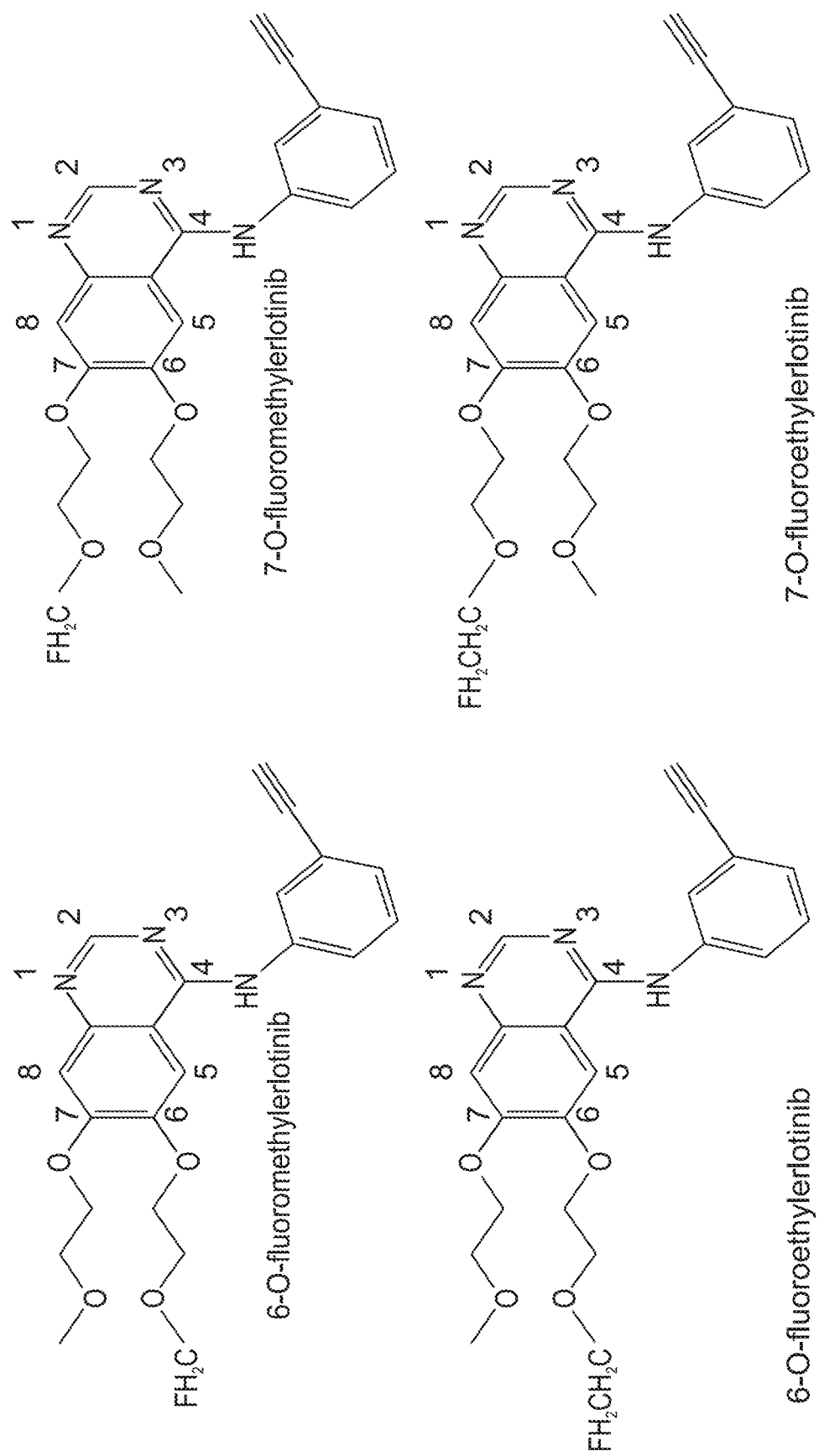

FIG. 1 presents the chemical structures of exemplary fluoro-containing erlotinib analogs, according to some embodiments of the present invention.

Figure 2:
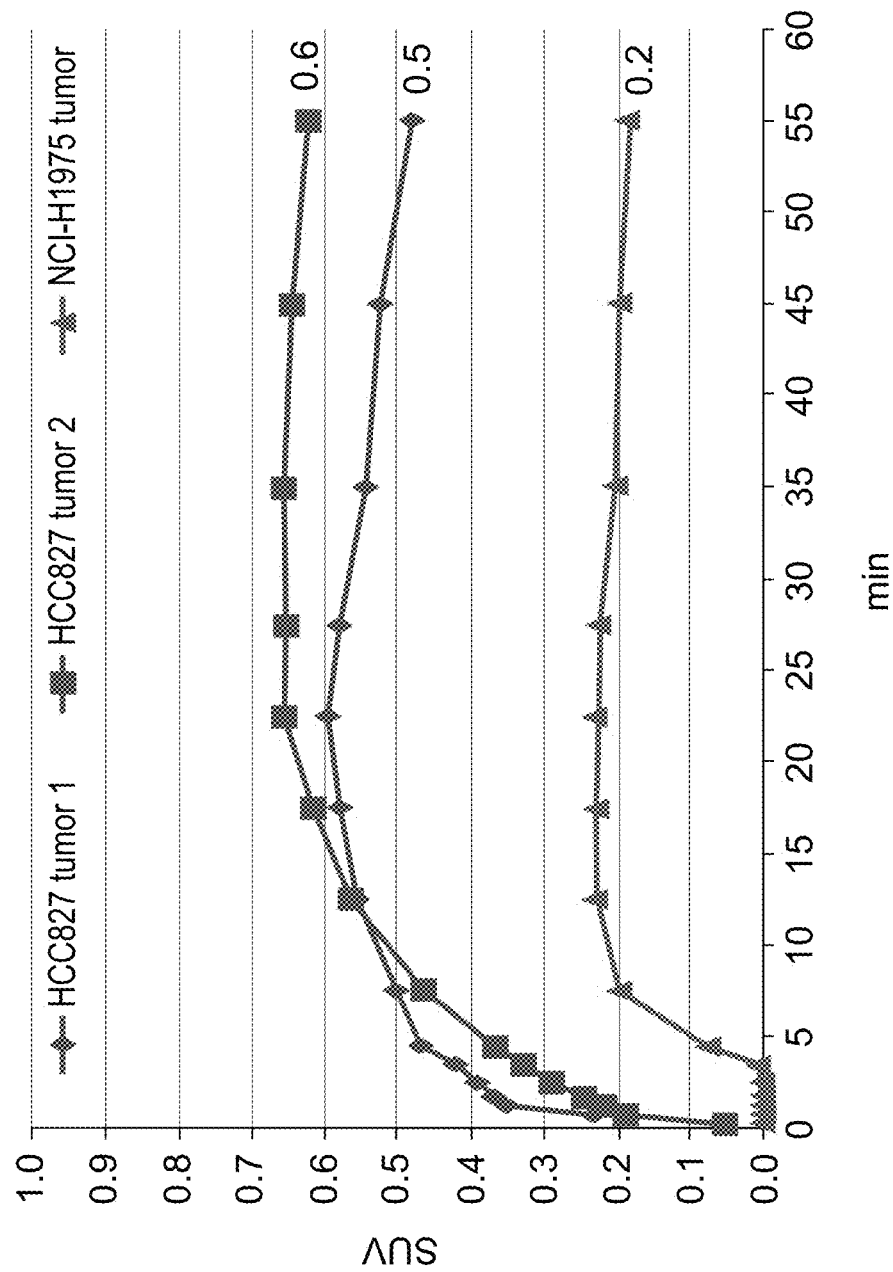

FIG. 2 presents comparative plots showing time-activity curves (TACs) of tumors following i.v. injection of [$^{18}$F]6-FEE into two mice bearing HCC827 tumor (red squares and blue diamonds) and one mouse bearing NCI-H1975 tumor (green triangles), presented as standard uptake values (SUV) as a function of time.

Figure 3:
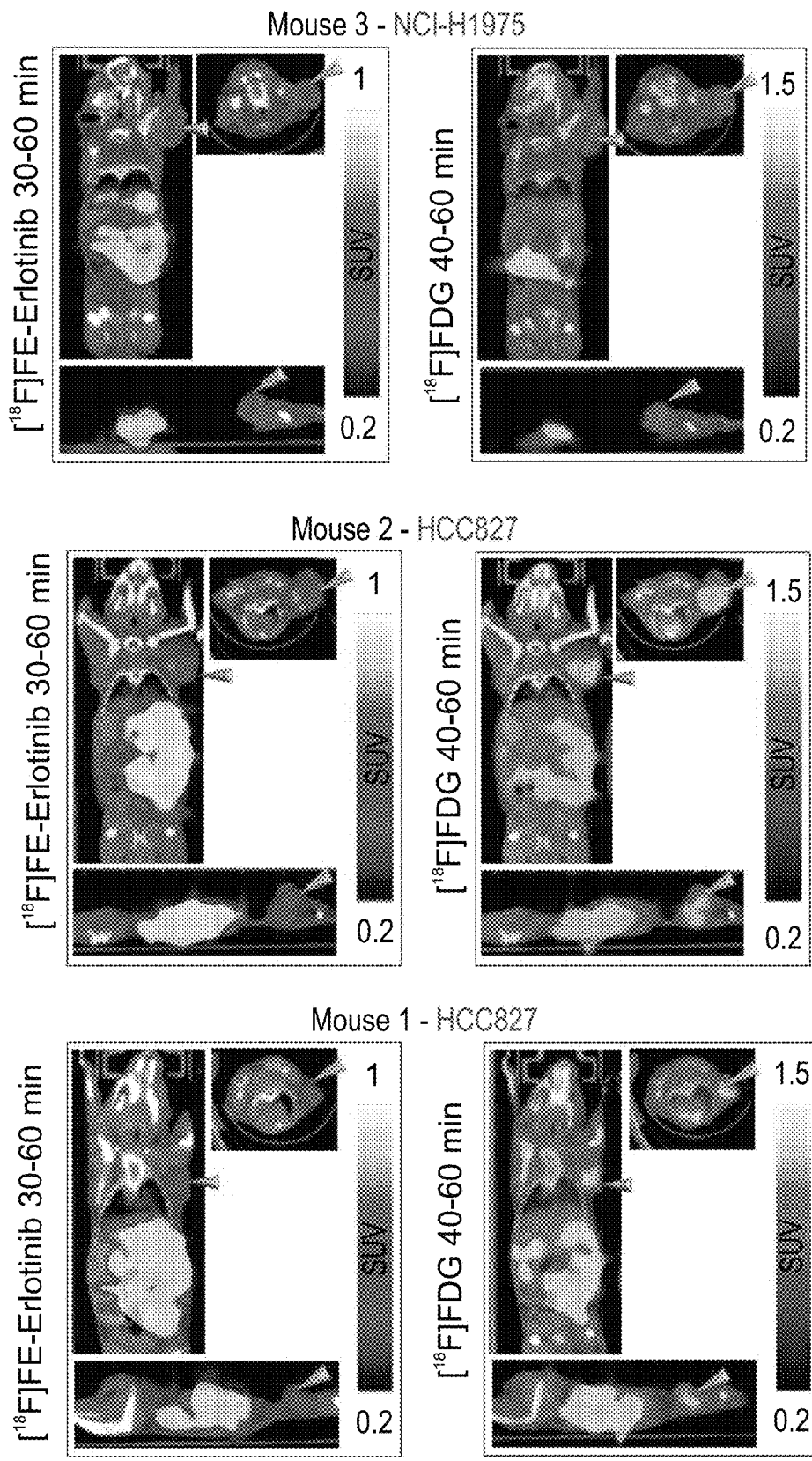

FIG. 3 presents PET/CT slice images of mice bearing HCC827 tumor (left and middle panels) and a mouse bearing NCI-H1975 tumor (right panel), at 30-60 minutes following i.v. injection of [$^{18}$F]6-FEE (top) and 40-60 minutes after injection of [$^{18}$F]FDG (bottom). Mice were scanned for 60 minutes following injection of [$^{18}$F]6-FEE, maintained at the same position for injection of [$^{18}$F]FDG, and scanned again 40 minutes later. Green arrows point at the location of tumors.

Figure 4:
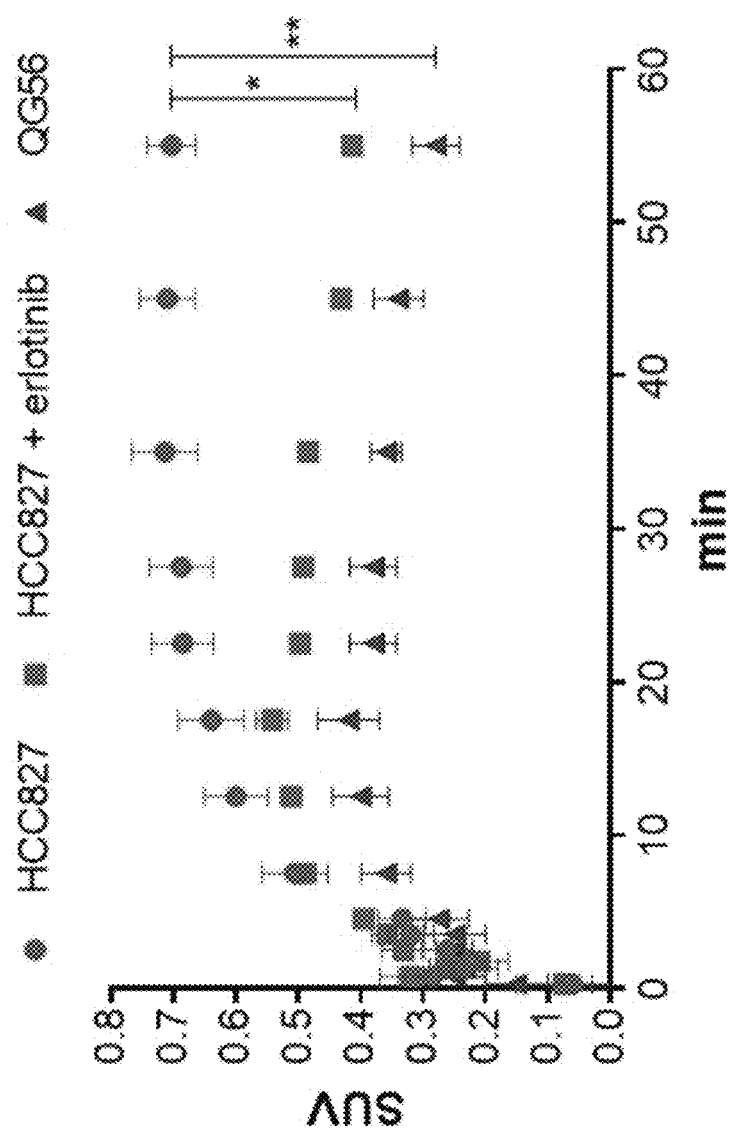

FIG. 4 presents comparative plots showing time-activity curves (TACs) of tumors following i.v. injection of [$^{18}$F]6-O-FEE (7.14±0.7 Mbq) into mice bearing QG56 tumor (blue triangles), into mice bearing HCC827 tumor (green circles) and into mice bearing HCC827 tumor pre-treated with non-labeled erlotinib in excess, presented as standard uptake values (SUV) as a function of time.

Figures 5A, 5B, 5C:
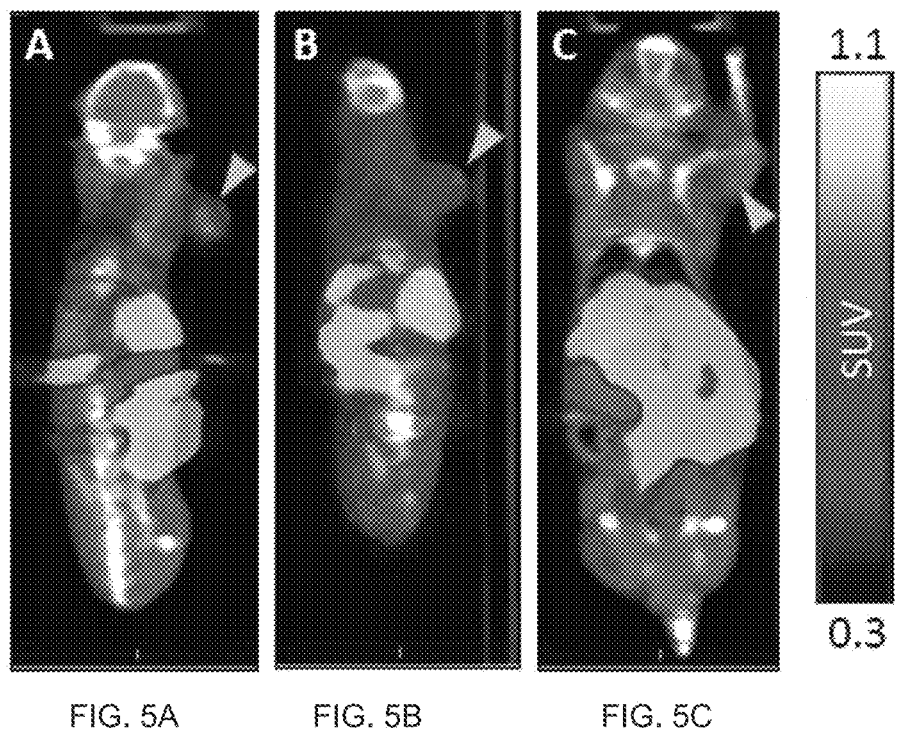

FIGS. 5A-C present PET/CT slice images of a mouse bearing an HCC827 tumor without (FIG. 5A) and following (FIG. 5B) pre-administration of non-labeled erlotinib in excess, and a mouse bearing a QG56 tumor (FIG. 5C), at 30-60 minutes following i.v. injection of [$^{18}$F]6-O-FEE. Green arrows point at the location of tumors.

DESCRIPTION OF SPECIFIC EMBODIMENTS OF THE INVENTION

The present invention, in some embodiments thereof, relates to radiopharmaceuticals and, more particularly, but not exclusively, to novel radiolabeled EGFR-TK inhibitors and their use as bioprobes for radioimaging (e.g., PET or SPECT) and in radiotherapy.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

As discussed hereinabove, non-invasive imaging methodologies are desirable for identifying patients with diseases or disorders that are associated with deregulated expression and/or activity of EGFR-TK (e.g., NSCLC tumors) that are responsive to treatment with inhibitors of EGFR-TK, and for monitoring EGFR mutational status before and/or during treatment.

As further discussed hereinabove, the ability of [$^{11}$C] erlotinib PET to non-invasively identify tumors that harbor activating mutations in the tyrosine kinase domain of the EGFR gene has been demonstrated in mouse models and in a limited number of clinical trials. However, owing to the relatively short half-life of carbon-11 (20.3 minutes), the use of [$^{11}$C]erlotinib PET as a non-invasive molecular imaging methodology limits its clinical application to medical centers with proximity to a cyclotron.

In a search for improved molecular imaging methodologies for determining and monitoring EGFR-TKI therapy in, for example, NSCLC patients, the present inventors have designed a novel family of halogen-containing compounds derived from erlotinib, and corresponding radiolabeled compounds bearing a radioactive halogen atom such as fluorine-18.

The newly designed compounds feature a halogen atom (e.g., fluorine) at a distal position with respect to the portions of the erlotinib molecule that bind to the ATP-binding pocket of the tyrosine kinase domain in EGFR-TK, and are therefore designed such that their affinity to the target is maintained.

Since radioactive halogens are typically characterized by a relatively long half-life (e.g., 109.8 minutes for fluorine-18) compared to that of carbon-11 (20.3 minutes) the newly designed radiolabeled compounds provide for substantially improved and broader clinical utilization of PET or SPECT (depending on the nature of the introduced radioactive halogen) as a non-invasive approach for identifying EGFR-TKI-responsive diseases or disorders (e.g., tumors) and for longitudinally monitoring EGFR-TKI therapy.

As described in further detail hereinbelow, a synthetic pathway has been designed for preparing fluorine-containing compounds derived from erlotinib, which serve as non-radiolabeled standards of fluorine-18-labeled compounds. In exemplary such fluorine-containing compounds, the methyl group at the terminus of the methoxyethoxy substituent at position 6 or 7 of the quinazoline ring in erlotinib is substituted by a fluoromethyl or a fluoroethyl group. See, FIG. 1. Introducing a halogen substituent at these positions allow using readily available starting materials such as 6-O-desmethylerlotinib and 7-O-desmethylerlotinib, respectively.

As further described in more detail hereinbelow, a fully automated synthetic route for preparing the fluorine-18 radiolabeled analogs of the fluorine-containing compounds presented in FIG. 1 has been designed. In some embodiments, fluorine-18 radiolabeled compounds are prepared in a one-step or a two-step radiosynthesis.

As demonstrated in the Examples section that follows, the overall biological performance of the fluorinated erlotinib analogs was tested in in vitro studies, using human NSCLC cell cultures. An exemplary fluorine-containing analog was shown to exhibit potency and selectivity to EGFR with various activating mutations similarly to erlotinib, thus demonstrating that the affinity and anti-proliferative activity are preserved in the modified compounds.

As further demonstrated in the Examples section that follows, an exemplary fluorine-18 radiolabeled erlotinib analog was successfully utilized in differentiating erlotinib-responsive NSCLC tumors in mice from non-responsive or resistant tumors, using PET. See, FIGS. 2, 3, 4 and 5A-C.

Embodiments of the present invention therefore relate to novel radiolabeled erlotinib analogs, and to uses thereof as radiopharmaceuticals in radioimaging, for identifying diseases and disorders that are responsive to treatment with small molecule inhibitors of EGFR-TK, and/or for monitoring such responsiveness during treatment, and/or in radiotherapy, for treating such diseases and disorders.

Herein throughout, the phrases "halogenated erlotinib analog", "halogenated erlotinib", "halogen-containing compound derived from erlotinib", "modified erlotinib", "erlotinib analog", and similar phrases are used interchangeably and describe compounds featuring a structure of erlotinib, as defined herein, to which one or more halogen atoms, or halogen-containing moieties, as described herein, are introduced. In some embodiments, these compounds feature a structure of erlotinib to which one or more halogen atoms, or halogen-containing moieties, as described herein, are introduced by replacing the terminal methyl of the methoxyethoxy substituents at positions 6 and 7 of the quinazoline ring of erlotinib. In some embodiments, these terms refer to compounds represented by Formula Ia or Ib, as described herein in any of the respective embodiments, and any combination thereof.

Herein throughout, the term "erlotinib" encompasses erlotinib per se as well as erlotinib derivatives, in which one or more of the hydrogens in the erlotinib is replaced by another substituent, in addition to the modification described herein for halogenated erlotinib compounds. In the context of some embodiments of the present invention, a halogenated erlotinib analog encompasses a halogenated erlotinib, modified to include a halogen atom as described herein, and a halogenated erlotinib derivative (as defined herein), modified to include a halogen atom as described herein. Exemplary halogenated erlotinib derivatives include compounds represented by Formula Ia and Ib as described herein, in which one or more of $R_1$-$R_{21}$ and Ra and Rb, if present, is/are other than hydrogen.

Herein throughout, the terms "halogen", "halogenated", "halogen-containing", and any other grammatical diversions thereof describing a compound, encompass the presence of one or more halogen atoms, including, for example, fluorine, bromine and/or iodine, in the compound.

As used herein, the phrase "radiolabeled compound" (type specified or not) describes a compound that comprises one or more radioactive atoms, as defined herein.

The phrase "radioactive atom" describes an atom with a specific radioactivity above that of background level for that atom. It is well known, in this respect, that naturally occurring elements are present in the form of varying isotopes, some of which are radioactive isotopes. The radioactivity of the naturally occurring elements is a result of the natural distribution of these isotopes, and is commonly referred to as a background radioactive level. However, there are known methods of enriching a certain element with isotopes that are radioactive. The result of such enrichment is a population of atoms characterized by higher radioactivity than a natural population of that atom, and thus the specific radioactivity thereof is above the background level.

Thus, the radioactive atoms or radiolabeled compounds of the present embodiments have a specific radioactivity that is higher than the corresponding non-radioactive atoms or non-labeled compounds, respectively, and can therefore be used as agents for radioimaging and radiotherapy.

Furthermore, the term "non-radioactive", as used herein with respect to an atom or group, refers to an atom or a group that does not comprise a radioactive atom and thus the specific radioactivity thereof is of a background level.

The term "radioactive", as used herein with respect to an atom or a group, refers to an atom or a group that comprises a radioactive atom and therefore the specific radioactivity thereof is above the background level.

Herein throughout, the terms "radiolabeled erlotinib", "radiolabeled erlotinib analog" and similar phrases describing a halogenated erlotinib analog as described herein which includes a radioactive halogen, refers to a halogenated erlotinib as defined herein, in which one or more of the halogen atoms is a radioactive halogen, e.g., radioactive fluorine, radioactive bromine and/or radioactive iodine, as defined herein. In some embodiments, these terms describe fluorine-18 radiolabeled erlotinib analogs.

Herein throughout, the terms "inhibitor of EGFR-TK", "EGFR-TK inhibitor" and "EGFR-TKI" are used interchangeably and describe small molecule inhibitors of EGFR-TK. Any of the known EGFR-TK inhibitors are encompassed by these terms, including, without limitation, erlotinib (Tarceva), afatinib, gefitinib (Iressa), lapatinib, and vandetanib.

Radiolabeled Compounds:

According to an aspect of some embodiments of the present invention, there are provided radiolabeled compounds which are radiolabeled analogs of erlotinib. These compounds possess the structural features of erlotinib, namely, a 4-anilinoquinazoline which is substituted, at the aniline ring, by an alkyne moiety, and at positions 6 and 7 of the quinazoline by 2-methoxyethoxy moieties. The compounds of the present embodiment, however, feature a radioactive halogen-containing moiety (e.g., a radioactive haloalkyl) instead of the terminal methyl at position(s) 6 and/or 7.

According to some of any of the embodiments of the present invention, the radiolabeled compounds are collectively represented by general Formula Ia or Ib:

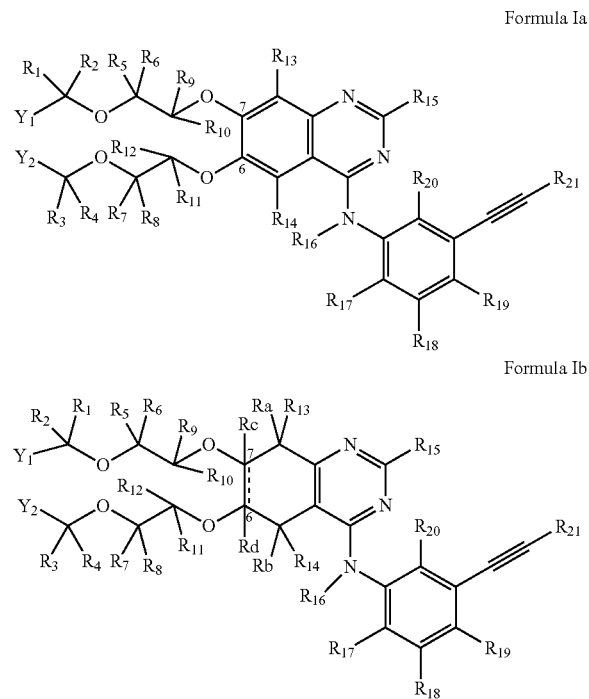

Formula Ia

Formula Ib wherein:

the dashed line in Formula Ib represents an optional unsaturated bond (that is, the dashed line may be absent, in which case the bond between the carbon atoms at positions 6 and 7 is a saturated bond; or the dashed line represents an unsaturated (e.g., double) bond between the carbon atoms at positions 6 and 7);

$R_1$-$R_{21}$, Ra and Rb are each independently selected from the group consisting of hydrogen, alkyl, cycloalkyl, aryl, heteroalicyclic, heteroaryl, alkoxy, aryloxy, thioalkoxy, thioaryloxy, hydroxyl, halogen, trihaloalkyl, trihaloalkoxy, amine, cyano, nitro, carbonyl, thiocarbonyl, carboxylate, thioacarboxylate, amide, thioamide, carbamate, thiocarbamate, alkaryl, aralkyl, sulfinyl, sylfonyl, sulfonate, and sulfonamide;

Rc and Rd are each absent, in case the dashed line represents an unsaturated (double) bond, or, in case the dashed line is absent, are each independently selected from the group consisting of hydrogen, alkyl, cycloalkyl, aryl, heteroalicyclic, heteroaryl, alkoxy, aryloxy, thioalkoxy, thioaryloxy, hydroxyl, halogen, trihaloalkyl, trihaloalkoxy, amine, cyano, nitro, carbonyl, thiocarbonyl, carboxylate, thioacarboxylate, amide, thioamide, carbamate, thiocarbamate, alkaryl, aralkyl, sulfinyl, sylfonyl, sulfonate, and sulfonamide; and $Y_1$ and $Y_2$ are each independently selected from the group consisting of hydrogen, alkyl, alkenyl, alkynyl, cycloalkyl, aryl, heteroalicyclic, heteroaryl, alkoxy, aryloxy, thioalkoxy, thioaryloxy, hydroxyl, halogen, trihaloalkyl, trihaloalkoxy, amine, cyano, nitro, carbonyl, thiocarbonyl, carboxylate, thioacarboxylate, amide, thioamide, carbamate, thiocarbamate, alkaryl, aralkyl, sulfinyl, sylfonyl, sulfonate, sulfonamide, a substituted or unsubstituted, saturated or unsaturated hydrocarbon chain of 1 to 20 carbon atoms, optionally interrupted by one or more heteroatoms, a radioactive halogen, and Q; and Q is a chemical moiety substituted by or terminating with a radioactive halogen (a radioactive halogen-containing moiety), provided that at least one of $Y_1$ and $Y_2$ is or comprises a radioactive halogen, as described herein.

According to some of any of the embodiments described herein, one or both of $Y_1$ and $Y_2$ is a radioactive halogen. In these embodiments, a terminal methyl of one or both of the 2-methoxyethoxy substituents at positions 6 and 7 of the quinazoline in erlotinib is replaced by a halomethyl, in which the halogen atom is a radioactive halogen atom, as described herein.

According to other embodiments of the present invention, one or both of $Y_1$ and $Y_2$ is a moiety other than methyl, that contains a radioactive halogen, and which is referred to herein as "Q". In these embodiments, one or both of $Y_1$ and $Y_2$ is such a moiety, and a terminal methyl of one or both of the 2-methoxyethoxy substituents at positions 6 and 7 of the quinazoline in erlotinib is replaced by this radioactive halogen-containing moiety.

In some embodiments, the radioactive halogen-containing moiety, Q, is an alkyl substituted by a radioactive halogen. In some of these embodiments, the alkyl is a lower alkyl, of 1 to 4 carbon atoms in length. In some embodiments, the alkyl can be a branched or linear alkyl. In some embodiments, the alkyl is substituted (in addition to the radioactive halogen) or unsubstituted (except for the radioactive halogen), and when substituted, the substituent can be as defined herein for $R_1$-$R_{21}$.

In some of any of the embodiments described herein, the alkyl terminates with the radioactive atom, such that the radioactive halogen substitutes a distal carbon of the alkyl with respect to its attachment point to the quinazoline.

In some of any of the embodiments described herein, Q is a methyl substituted by the radioactive halogen. Alternatively, Q is an ethyl, propyl or butyl, substituted by the radioactive halogen. For example, in some embodiments, Q is 2-haloethyl or 3-halopropyl, or 2-halopropyl, or 4-halobutyl, or 3-halobutyl, or 2-halobutyl, each of which features a radioactive halogen as the halo substituent. In some embodiments, Q is a halomethyl, a 2-haloethyl, a 3-halopropyl or a 4-halobutyl, each of which features a radioactive halogen as the halo substituent.

In some embodiments, the radioactive halogen-containing moiety, Q, is a saturated or unsaturated hydrocarbon chain of 2 to 20 carbon atoms, optionally interrupted by one or more heteroatoms, which is substituted by or terminating with the radioactive halogen, and may optionally be substituted by one or more additional substituents (as depicted in Formulae Ia and Ib for $R_1$-$R_{21}$).

Herein, the term "hydrocarbon" describes an organic moiety that includes, as its basic skeleton, a chain of carbon atoms, also referred to herein as a backbone chain, substituted mainly by hydrogen atoms. The hydrocarbon can be saturated or unsaturated, be comprised of aliphatic, alicyclic and/or aromatic moieties, and can optionally be substituted by one or more substituents (other than hydrogen). A substituted hydrocarbon may have one or more substituents, whereby each substituent can independently be, for example, alkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, azide, sulfonamide, carboxy, thiocarbamate, urea, thiourea, carbamate, amide, and hydrazine, and any other substituents as described herein (for example, as defined herein for $R_1$-$R_{21}$).

The hydrocarbon moiety can optionally be interrupted by one or more heteroatoms, including, without limitation, one or more oxygen, nitrogen (substituted or unsubstituted, as defined herein for —NR'—) and/or sulfur atoms.

In some embodiments of any of the embodiments described herein relating to Q being or comprising a hydrocarbon, the hydrocarbon is not interrupted by any heteroatom, nor does it comprise heteroatoms in its backbone chain, and can be an alkylene chain, or be comprised of alkyls, cycloalkyls, aryls, alkaryls, aralkyls, alkenes and/or alkynes, as defined herein, covalently attached to one another in any order.

In some of these embodiments, the hydrocarbon is such that one or more of the groups composing the backbone chain, as described herein, is substituted by a radioactive halogen.

In some of these embodiments, the hydrocarbon is such that a terminal group in the backbone chain, for example, an alkyl, alkenyl or alkynyl, is substituted at its terminus by a radioactive halogen.

In some of these embodiments, Q is an alkylene chain.

The term "alkylene" describes a saturated aliphatic hydrocarbon group, as this term is defined herein. This term is also referred to herein as "alkyl".

In some embodiments, one or more carbon atoms in the alkylene chain is substituted by a radioactive halogen.

In some embodiments, the terminal carbon in the alkylene (at the distal end relative to the point of its attachment to the quinazoline ring) is substituted by a radioactive halogen.

In some embodiments, when Q is an alkylene chain, Q can be represented by (CR'R")nX, wherein R' and R" are as defined herein, and each independently can be, for example, hydrogen, alkyl, cycloalkyl, aryl, heteroalicyclic, heteroaryl, alkoxy, aryloxy, thioalkoxy, thioaryloxy, hydroxyl, halogen, trihaloalkyl, trihaloalkoxy, amine, cyano, nitro, carbonyl, thiocarbonyl, carboxylate, thioacarboxylate, amide, thioamide, carbamate, thiocarbamate, alkaryl, aralkyl, sulfinyl, sylfonyl, sulfonate, and sulfonamide; n is an integer of from 2 to 20; and X is the radioactive halogen.

According to these embodiments, Q is an alkylene chain that is composed of 2-20 (CR'R") units.

R' and R" in each of these units can independently be the same or different.

In some embodiments, in at least one of the CR'R" units, R' and R" are each hydrogen.

In some of these embodiments, in all of the CR'R" units in the alkylene chain, each of R' and R" is hydrogen. According to these embodiments, Q is s an unsubstituted alkylene chain that terminates with a radioactive halogen.

When one or both of R' and R" in one of more of the CR'R" units is other than hydrogen, Q is referred to as a substituted alkylene chain that terminated with a radioactive halogen.

In some of these embodiments, n is an integer ranging from 2 to 10, or from 2 to 6, or from 2 to 4.

In some of these embodiments, n is 2.

In some embodiments of any of the embodiments described herein relating to Q as being or comprising a hydrocarbon chain, the hydrocarbon chain is interrupted by one or more heteroatoms.

Exemplary such hydrocarbons comprise one or more alkylene glycol groups or derivatives thereof.

As used herein, the term "alkylene glycol" describes a —[O—(CR'R")z]y- group, with R' and R" being as defined herein (and/or as defined herein for $R_1$-$R_{21}$), and with z being an integer of from 1 to 10, preferably, from 2 to 6, more preferably 2 or 3, and y being an integer of 1 or more. Preferably R' and R" are both hydrogen. When z is 2 and y is 1, this group is ethylene glycol. When z is 3 and y is 1, this group is propylene glycol. When y is greater than 1, this group is also referred to herein as "alkylene glycol chain".

When y is greater than 4, the alkylene glycol chain is also referred to herein as poly(alkylene glycol) moiety. In some embodiments of the present invention, a poly(alkylene glycol) moiety can have from 4 to 10 alkylene glycol groups, such that y is, for example, 4 to 10.

In some embodiments, the hydrocarbon chain is or comprises one or more alkylene glycol derivatives, in which one or more of the oxygen atoms is replaced by a sulfur atom and/or a —NR'— group, as defined herein, and/or one or more of R' and R" in one or more unit is other than hydrogen.

According to some of any of the embodiments described herein, Q is or comprises one or more alkylene glycol groups, as defined herein, and terminates with a radioactive halogen, as described herein, such that a radioactive halogen is attached to the alkylene glycol group or to a terminal alkylene glycol group in case where y is greater than 1. Alternatively, R' and R" in one of the one or more alkylene glycol groups is a radioactive halogen.

The number of alkylene glycol groups can range from 1 to 20, or from 1 to 10, or from 1 to 8, or from 1 to 6, or from 1 to 4, or from 1 to 3, or from 1 to 2.

When 2 or more alkylene glycol units are present, the groups can be the same or different.

For example, R' and R" in each of these groups can independently be the same or different. Alternatively, or in addition, one or more alkylene glycol groups can differ from one another when one or both of the oxygen atoms is replaced by —NR'— or —S— in one or more units.

In some embodiments, in at least one, or in all of, the alkylene glycol units, R' and R" are each hydrogen.

In some of these embodiments, in all of the alkylene glycol units, each of R' and R" is hydrogen.

According to some of these embodiments, Q is or comprises an unsubstituted alkylene glycol chain that terminates with a radioactive halogen.

In some embodiments, one or both of R' and R" in one of more of the alkylene glycol groups is other than hydrogen, and Q is or comprises a substituted alkylene glycol chain that terminates with a radioactive halogen.

In some of any of the embodiments described herein for a hydrocarbon, the hydrocarbon moiety has from 2 to 20 carbon atoms, or 2 to 10 carbon atoms, or 2 to 8 carbon atoms, or 2 to 6 carbon atoms, or 2 to 4 carbon atoms.

In some of any of the embodiments described herein, each of $R_1$-$R_4$ is hydrogen.

In some of any of the embodiments described herein, each of $R_5$-$R_{12}$ is hydrogen.

In some of any of the embodiments described herein, each of $R_{17}$-$R_{21}$ is hydrogen.

In some of any of the embodiments described herein, the radiolabeled compound is represented by Formula Ia.

In some of these embodiments, each of $R_1$-$R_4$ is hydrogen; and/or each of $R_5$-$R_{12}$ is hydrogen; and/or each of $R_{13}$-$R_{16}$ is hydrogen; and/or each of $R_{17}$-$R_{21}$ is hydrogen.

In some of these embodiments, each of $R_1$-$R_{21}$ is hydrogen. According to these embodiments, the radiolabeled compound is an analog of erlotinib (non-derivatized).

In some of these embodiments, Q is a methyl substituted by a radioactive halogen, namely, —$CH_2$—X, with X being the radioactive halogen (e.g., fluorine-18).

Alternatively, the radiolabeled compound is represented by Formula Ib.

In some of these embodiments, each of $R_1$-$R_4$ is hydrogen; and/or each of $R_5$-$R_{12}$ is hydrogen; and/or each of $R_{13}$-$R_{16}$, Ra, Rb, Rc (if present) and Rd (if present) is hydrogen; and/or each of $R_{17}$-$R_{21}$ is hydrogen.

In some of these embodiments, each of Ra, Rb, Rc, Rd and $R_1$-$R_{21}$ is hydrogen. In some of these embodiments, Q is a methyl substituted by a radioactive halogen, namely, —$CH_2$—X, with X being the radioactive halogen (e.g., fluorine-18).

In alternative embodiments, compounds represented by Formula Ia or Ib feature a radioactive halogen-containing moiety at positions of the erlotinib skeleton other than $Y_1$ and $Y_2$. In some of these embodiments, none of $Y_1$ and $Y_2$ is or comprises a radioactive halogen, and one or more of $R_1$-$R_{21}$ in Formula Ia, or $R_1$-$R_{21}$, Ra and Rb in Formula Ib, is or comprises a radioactive halogen.

Exemplary such compounds are compounds as described in U.S. Pat. No. 8,575,339, in which one or more of the fluoro substituents is replaced by a radioactive halogen (e.g., a radioactive fluorine). Methods of introducing a radioactive halogen as a substituent on the aniline ring can be, for example, as described in U.S. Pat. Nos. 6,126,917, 6,562,319, 7,172,749, and 8,461,166. U.S. Pat. Nos. 8,575,339, 6,126,917, 6,562,319, 7,172,749, and 8,461,166 are incorporated by reference as if fully set forth herein.

The Radioactive Halogen:

In some of any of the embodiments described herein, the radioactive halogen is a radioactive fluorine.

In some of any of the embodiments described herein, the radioactive halogen is fluorine-18, which is also referred to herein as $^{18}F$, or as $[F^{18}]$.

Fluorine-18 radiolabeled compounds are known as useful as radioimaging agents for PET.

In some of any of the embodiments described herein, the radioactive halogen is a radioactive bromine.

Exemplary radioactive bromine atoms include, but are not limited to, bromine-76 and bromine-77.

Bromine-76 radiolabeled compounds can be used for PET radioimaging.

Bromine-77 radiolabeled compounds can be used for radiotherapy.

In some of any of the embodiments described herein, the radioactive halogen is a radioactive iodine.

Exemplary radioactive iodine atoms include, but are not limited to, iodine-123, iodine-124, and iodine-131.

Iodine-123 radiolabeled compounds can be used for SPECT radioimaging.

Iodine-124 radiolabeled compounds can be used for both PET radioimaging and/or radiotherapy.

Iodine-131 radiolabeled compounds can be used for radiotherapy.

Any other radioactive isotopes of fluorine, bromine and iodine are also contemplated.

Radioactive isotopes of fluorine, bromine and iodine can be commercially available, or can be generated by methods known in the art.

An exemplary method of generating radioactive fluorine is described in the Examples section that follows.

Radiosyntheses:

The radiolabeled compounds as described herein are readily synthesizable, using, for example, one-step or two-step radiosyntheses.

In some of any of the embodiments described herein, a process of preparing a radiolabeled compound as described herein is effected by reacting a compound represented by Formula IIa or IIb:

Formula IIa

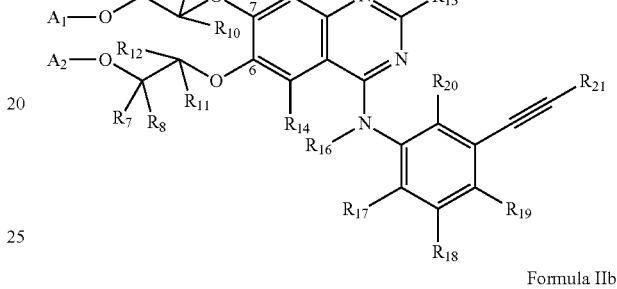

Formula IIb

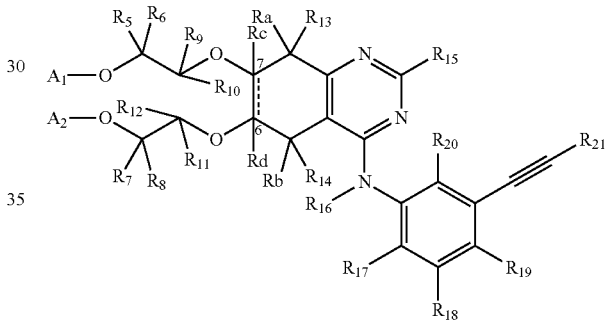

wherein:

$A_1$ is —$CR_1R_2B_1$, —$CR_1R_2Q_1W_1$, or forms with the oxygen to which it is attached $W_1$; and $A_2$ is —$CR_3R_4B_2$, —$CR_3R_4Q_2W_2$, or forms with the oxygen to which it attached $W_1$;

$B_1$ and $B_2$ are each independently as defined herein for $R_1$-$R_{21}$;

$Q_1$ and $Q_2$ are each independently as defined herein for Q or is absent; $W_1$ and $W_2$ are each independently a reactive group; and all other variables are defined herein for Formula Ia or Ib, respectively, provided that at least one of $A_1$ and $A_2$ forms with the oxygen to which it is attached, or comprises, said reactive group ($W_1$ and/or $W_2$), with a compound represented by Formula III(1) and/or III(2):

$$L_A\text{-}(CR_1R_2)m(Q)k\text{-}Z \qquad \text{Formula III(1)}$$

$$L_A\text{-}(CR_3R_4)m(Q)k\text{-}Z \qquad \text{Formula III(2)}$$

wherein:

$L_A$ is a leaving group or is absent;

Z is said radioactive halogen;

m is 0 or 1; and k is 0 or 1.

Q in any one of Formulae III(1) and (III)2 is as defined herein for Q.

For preparing radiolabeled compounds represented by Formula Ia as described herein, the starting material is a compound represented by Formula IIa.

For preparing radiolabeled compounds represented by Formula Ib as described herein, the starting material is a compound represented by Formula IIb.

The compound of Formula III(1) is reacted with a compound represented by Formula IIa or IIb in which $A_1$ forms a part of, or comprises, the reactive group $W_1$ ($A_1$ is —$CR_1R_2Q_1W_1$, or forms with the oxygen to which it is attached $W_1$), and a compound represented by Formula III(2) is reacted with a compound represented by Formula IIa or IIb in which $A_2$ forms a part of, or comprises, the reactive group $W_2$ ($A_2$ is —$CR_3R_4Q_2W_2$, or forms with the oxygen to which it is attached $W_2$).

The starting material of Formula IIa or IIb is selected so as to provide a radiolabeled compound is which the radioactive halogen or a moiety containing same is introduced to the substituent as position 6 and/or 7, by selecting $A_1$ and/or $A_2$ which can participate in a chemical reaction with a compound of Formula III(1) and/or Formula III(2), respectively. If the radioactive halogen or a moiety containing same is to be introduced at position 7, then $A_1$ forms a part of, or comprises the reactive group. Alternatively, or is addition, if the radioactive halogen or a moiety containing same is to be introduced at position 6, then $A_2$ forms a part of, or comprises the reactive group.

Thus, when $A_1$ forms the reactive group $W_1$ or is —$CR_1R_2Q_1W_1$, a compound of Formula IIa or IIb is reactive towards a chemical reaction with a compound of Formula III(1), to thereby provide a compound of Formula Ia or Ib in which $Y_1$ is or comprises a radioactive halogen. When $A_2$ forms the reactive group $W_2$ or is —$CR_3R_4Q_2W_2$, a compound of Formula IIa or IIb is reactive towards a chemical reaction with a compound of Formula III(2), to thereby provide a compound of Formula Ia or Ib in which $Y_2$ is or comprises a radioactive halogen.

In some of any of the embodiments described herein, $A_1$ forms together with the oxygen atom to which it is attached the reactive group $W_1$ and/or $A_2$ forms together with the oxygen atom to which it is attached the reactive group(s) $W_2$.

In some of any of these embodiments, the reactive groups, $W_1$ and/or $W_2$ and $L_A$ are selected suitable to participate in a displacement reaction in which —$(CR_1R_2)m(Q)k$-Z displaces $A_1$ and/or $(CR_3R_4)m(Q)k$-Z displaces $A_2$.

In some of any of these embodiments, $W_1$ and W2 are nucleophilic groups and $L_A$ is a leaving group and the displacement reaction is a nucleophilic substitution.

In some of these embodiments, when $A_1$ forms with the oxygen to which it is attached the $W_1$ nucleophilic group, then m in Formula III(1) is 1.

In some of these embodiments, when A2 forms with the oxygen to which it is attached the $W_2$ nucleophilic group, then m in Formula III(2) is 1.

In embodiments where one or both of $A_1$ and $A_2$ forms with the oxygen to which it is attached the reactive groups $W_1$ and/or $W_2$, respectively, a moiety of Formula III(1) and/or Formula III(2), which contains a radioactive halogen, is first prepared, and is then reacted with a compound of Formula IIa or IIb to provide compound Ia or Ib, respectively.

According to these embodiments, the radiosynthesis is a two-step radiosynthesis, in which in the first step a radiolabeled compound of Formula III(1) or III(2) is prepared, and in the second step, it is reacted with a compound of Formula IIa or IIb in which $A_1$ and/or $A_2$ form the reactive nucleophilic group(s) $W_1$ and/or $W_2$.

In some of any of the embodiments where one or both of $A_1$ and $A_2$ forms with the oxygen to which it is attached the reactive groups $W_1$ and/or $W_2$, the process further comprises prior to reacting a compound of Formula IIa or IIb with a compound of Formula III(1) and/or Formula III(2), preparing a radiolabeled compound of Formula III(1) and/or III(2).

In some embodiments, a preparation of a compound of Formula III(1) or III(2) is effected by reacting a radioactive halide with a compound of Formula IV(1) or IV(2):

   Formula IV(1)

   Formula IV(2)

with $L_B$ being a leaving group, as defined herein, and can be the same as or different from $L_A$.

The reagent used for introducing the radioactive halogen, of Formula III(1) or III(2), and the compounds of Formula IV(1) and IV(2), are selected so as to provide a compound of Formula Ia or Ib, by featuring $R_1$-$R_4$ and Q of the end product.

In exemplary embodiments, one or both of $A_1$ and $A_2$ is hydrogen, forming a hydroxy reactive group.

In exemplary embodiments, k is 0, and the displacement reaction results in introduction of a radiolabeled halomethyl group, which displaces $A_1$ so as provide a radiolabeled halomethoxy group instead of the terminal methoxy at position 6 and/or 7. In these embodiments, in the compound of Formula Ia or Ib, $Y_1$ and/or $Y_2$ is a radioactive halogen.

In exemplary embodiments, k is 1 and the displacement reaction results in introduction of a radiolabeled moiety, Q, which comprises or terminates with the radioactive halogen Z.

In exemplary embodiments, Q is an alkyl and the displacement reaction results in introduction of a radiolabeled haloalkyl group of 2 or more carbon atoms, which displaces $A_1$ so as provide a radiolabeled haloalkoxy group of 2 or more carbon atoms instead of the terminal methoxy at position 6 and/or 7. In these embodiments, in the compound of Formula Ia or Ib, $Y_1$ and/or $Y_2$ is Q, and Q is an alkyl that comprises (is substituted by or terminates with) a radioactive halogen, as described herein.

In exemplary embodiments, a reagent of Formula III(1) can be represented by the following formula:

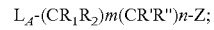

and a reagent of Formula III(2) can be represented by the following formula:

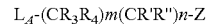

wherein $R_1$-$R_4$, R' and R" and n are as described herein.

In some of any of the embodiments described herein, $A_1$ and/or $A_2$ comprise(s) the reactive group $W_1$ and/or $W_2$, respectively, such that $A_1$ is —$CR_1R_2Q_1W_1$ and/or $A_2$ is —$CR_3R_4Q_2W_2$.

In some of any of these embodiments, the reactive groups, $W_1$ and/or $W_2$ and $L_A$ are selected suitable to participate in a displacement reaction in which the radioactive halogen Z displaces $W_1$ and/or $W_2$.

In some of these embodiments, the displacement reaction is a nucleophilic substitution in which a radioactive halide displaces the reactive group, $W_1$ and/or $W_2$, so as to afford a radioactive halogen substituent at the respective position(s).

In some of any of these embodiments, $W_1$ and $W_2$ are leaving groups and $L_A$ is such that together with Z generates a radioactive halide. $L_A$ can be, for example, a cation, for example, $M^+$, with M being, for example, an alkali metal, forming $M^+Z^-$ as a reagent of Formula III(1) or (III)2. Alternatively, $L_A$ is absent or can be regarded as an electron that generates the radioactive halide.

In some of these embodiments, when $A_1$ is $—CR_1R_2Q_1W_1$, then m and k in Formula III(1) are both 0.

In some of these embodiments, when $A_2$ is $—CR_3R_4Q_2W_2$, then m and k in Formula III(2) are both 0.

In some of these embodiments, the radiosynthesis is a one-step radiosynthesis, in which once a radioactive halide is generated, it is reacted with a compound of Formula IIa or IIb, to thereby provide a radiolabeled compound of Formula Ia or Ib, respectively.

In embodiments where one or both of $A_1$ and $A_2$ comprises a reactive group $W_1$ and/or $W_2$, a compound of Formula IIa or IIb in which $A_1$ is $—CR_1R_2Q_1W_1$ and/or $A_2$ is $—CR_3R_4Q_2W_2$ is first prepared, and is then reacted with a compound of Formula III(1) or III(2), to thereby provide a compound of Formula Ia or Ib, respectively.

In some of any of the embodiments described herein for $A_1$ and/or $A_2$ which comprise a reactive group, the process further comprises, prior to reacting a compound of Formula IIa or IIb with a compound of Formula III(1) and/or III(2), preparing a compound of Formula IIa or IIb in which $A_1$ is $—CR_1R_2Q_1W_1$ and/or $A_2$ is $—CR_3R_4Q_2W_2$.

In some of these embodiments, a compound of Formula IIa or IIb in which $A_1$ is $—CR_1R_2Q_1W_1$ is prepared by reacting a compound of Formula IIa or IIb in which $A_1$ forms a reactive group with an oxygen them to which it is attached, as described herein in any of the respective embodiments, with a compound of the following formula:

$L_C\text{-}CR_1R_2Q_1W_1,$ wherein $L_C$ is a leaving group, as described herein.

In some embodiments, the reaction is a displacement reaction, e.g., a nucleophilic substitution, in which $—CR_1R_2Q_1W_1$ displaces $A_1$.

In some of these embodiments, a compound of Formula IIa or IIb in which $A_2$ is $—CR_3R_4Q_2W_2$ is prepared by reacting a compound of Formula IIa or IIb in which $A_2$ forms a reactive group with an oxygen them to which it is attached, as described herein in any of the respective embodiments, with a compound of the following formula:

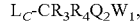

$L_C\text{-}CR_3R_4Q_2W_1,$ wherein $L_C$ is a leaving group, as described herein.

In some embodiments, the reaction is a displacement reaction, e.g., a nucleophilic substitution, in which $—CR_3R_4Q_2W_2$ displaces $A_1$.

In some of any of the embodiments described herein for $A_1$ and/or $A_2$ which comprise a reactive group, the reactive group, $W_1$ or $W_2$ can form part of $Q_1$ or $Q_2$, respectively. For example, when Q is a hydrocarbon chain interrupted by one or more heteroatoms, such heteroatoms can act as reactive group $W_1$ or $W_2$. When Q is a substituted hydrocarbon chain, one or more of the substituents can be a reactive group $W_1$ or $W_2$. When Q is an alkylene glycol chain, the reactive group can be a terminal hydroxy group of the alkylene glycol from which it is derived.

For any of the embodiments described herein, a radioactive halide of choice, e.g., $[^{18}F]^-$, $[^{76}Br]^-$, $[^{77}Br]^-$, $[^{123}I]^-$, $[^{124}I]^-$ or $[^{131}I]^-$, can be generated by methods known in the art, or can be purchased from known vendors, either per se, or as a reagent generating same (for example, $M^+Z^-$, as described herein).

As used herein throughout, the phrase "leaving group" describes a labile atom, group or chemical moiety that readily undergoes detachment from an organic molecule during a chemical reaction, while the detachment is facilitated by the relative stability of the leaving atom, group or moiety thereafter. Typically, any group that is the conjugate base of a strong acid can act as a leaving group. Representative examples of suitable leaving groups according to the present invention therefore include, without limitation, carboxylate (e.g., acetate), thiocarboxylate, sulfate (e.g., tosylate, mesylate), sulfonate (e.g., triflate), sulfinate, thiosulfate, thiosulfonate, thiosulfinate, sulfoxide, alkoxy, halogen (preferably bromo or iodo), amine, sulfonamide, carbamate, thiocarbamate, azide, phosphonyl, phopshinyl, phosphate, cyanate, thiocyanate, nitro and cyano, as these terms are defined herein.

In some embodiments, one or more of the leavings groups described herein can be a sulfate (e.g., tosylate or mesylate or nosylate), a sulfonate (e.g., triflate), bromo and/or iodo.

The leaving groups referred to herein as, for example, $L_A$, $L_B$, $L_C$, $L_1$, $L_2$ or L, can be the same or different, and can be selected suitable for the reactions described with respect thereto.

As used herein, the phrase "reactive group" describes a chemical group that is capable of undergoing a chemical reaction that typically leads to a bond formation. The bond, according to the present invention, is preferably a covalent bond. In some embodiments, the chemical reactions that lead to a bond formation include, for example, nucleophilic and electrophilic substitutions, nucleophilic and electrophilic addition reactions, addition-elimination reactions, cycloaddition reactions, rearrangement reactions and any other known organic reactions that involve a reactive group.

In some embodiments, a reactive group as described herein is a chemical group that is capable of participating in a nucleophilic substitution, as a nucleophilic group or alternatively, as a leaving group.

In some embodiments, the reactive group is a nucleophilic group.

Representative examples of suitable nucleophilic groups according to the present invention include, without limitation, hydroxy, amine, alkoxy, aryloxy, thiohydroxy, thioalkoxy, thioaryloxy, urea, and thiourea, as these terms are defined hereinabove.

In some embodiments, the reactive group is a leaving group, as described herein.

In some embodiments, the reactive group can be, as non-limiting examples, amine, halogen, acyl-halide, sulfonate, sulfoxides, phosphate, hydroxy, alkoxy, aryloxy, thiohydroxy, thioalkoxy, thioaryloxy, cyano, nitro, azo, isocyanate, sulfonamide, C-carboxylate, O-carboxylate, N-thiocarbamate, O-thiocarbamate, urea, thiourea, O-carbamate, N-carbamate, C-amide, N-amide, guanyl, alkene, alkyne, aryl, guanidine and hydrazine, as these terms are defined hereinabove.

For any of the embodiments of a process as described herein, the reactions described herein are performed at conditions (e.g., temperature, solvent, additional reagents such as acids, bases and the like) suitable for performing the displacement reactions described herein. Conditions suitable for the reactive groups, radioactive halides and leaving groups utilized can be readily selected by those skilled in the art.

In some of any of the embodiments described herein, once a radiolabeled compound of Formula Ia or Ib is prepared, it can be stored in a suitable carrier, as described herein, for up to several hours, depending on the radioactive halogen it comprises, before it is used in any of the radioimaging or radiotherapy methods described herein.

Radiolabeled compounds as described herein, which comprise a radioactive fluorine, e.g., fluorine-18, can be used up to about 4 hours upon being prepared.

Radiolabeled compounds as described herein, which comprise a radioactive bromine, e.g., bromine-76 or bromine-77, can be used up to about 48 hours, or 24 hours, upon being prepared.

Radiolabeled compounds as described herein, which comprise radioactive iodine, e.g., iodine-123, iodine-124 or iodine-131, can be used up to several days upon being prepared (e.g., 2, 3, or 4 days, and even upon longer time periods).

Radioimaging:

The radiolabeled compounds herein described can be used as radioimaging agents. Fluorine-18 labeled, bromine-76 labeled and iodine-124 labeled compounds of the invention, for example, can be used as biomarkers for PET radioimaging, whereas iodine-123 labeled compounds, for example, of the invention can be used as biomarkers for SPECT radioimaging.

Thus, according to some of any of the embodiments of the present invention, the radiolabeled compounds as described herein are for use in radioimaging, or in a method of radioimaging, or as radioimaging agents.

According to some of any of the embodiments of the present invention, the radiolabeled compounds as described herein are for use in the manufacture of a radioimaging agent. The radioimaging agent is for use in a method of radioimaging as described herein.

According to some of any of the embodiments of the present invention, the radioimaging is effected by administering to the patient any of, for example, the fluorine-18, bromine-76, iodine-123 or iodine-124 radiolabeled compounds described herein (or any other halogen-containing erlotinib compound in which the halogen is a radioactive halogen isotope suitable for nuclear imaging) and employing a suitable nuclear imaging technique, such as positron emission tomography or single photon emission computed tomography, for monitoring a distribution of the compound within the body or within a portion thereof.

Accordingly, according to an aspect of some embodiments of the present invention there is provided a method of radioimaging, which comprises administering to the patient any of, for example, the fluorine-18, bromine-76, iodine-123 or iodine-124 radiolabeled compounds described herein (or any other halogen-containing erlotinib compound in which the halogen is a radioactive halogen isotope suitable for nuclear imaging) and employing a suitable nuclear imaging technique, such as positron emission tomography or single photon emission computed tomography, for monitoring a distribution of the compound within the body or within a portion thereof.

Nuclear imaging dosing depends on the affinity of the compound to its receptor, the isotope employed and the specific activity of labeling. Persons ordinarily skilled in the art can easily determine optimum nuclear imaging dosages and dosing methodology.

In some embodiments, a radioimaging method as described herein is useful for monitoring or determining a level and/or distribution and/or mutational status of epidermal growth factor receptor (EGFR) within the body of the patient.

In some embodiments, the level and/or distribution of the radiolabeled compound in the patient's body or a portion thereof is indicative of the level and/or distribution of the epidermal growth factor receptor in the patient's body or the portion thereof.

Such a radioimaging is useful for determining if the patient suffers from a disease or disorder that is associated with deregulated expression and/or activity of EGFR.

Herein, the phrase "deregulated expression and/or activity" of EGFR describes aberrant, or abnormal, expression and/or activity of EGFR.

In some embodiments, this phrase describes upregulation of EGFR, for example, overexpression of EGFR and/or overactivity of EGFR.

In some embodiments, an overactivity of EGFR is reflected by constitutive activity of EGFR.

In some embodiments, an overactivity of EGFR is reflected by increased activity of the EGFR tyrosine kinase.

As discussed in detail hereinabove, and is known in the art, EGFR-TK inhibitors such as erlotinib are characterized by an affinity to the ATP binding site of EGFR tyrosine kinases.

The radiolabeled compounds as described herein are therefore preferably characterized by high affinity to EGFR-TK. Cells, tissues or organs which feature an increased activity of EGFR-TK are therefore assumed to result in a higher uptake of the radiolabeled compounds of the present embodiments, compared to those which do not feature overactivity of EGFR-TK (and also to those which feature overexpression of EGFR but without overactivity of EGFR-TK), such that an accumulation (a level) of the radiolabeled compound at certain cells, tissues and or organs of a patient (distribution) is indicative of an increased activity of EGFR-TK in these cells, tissues or organs, and hence of a disease or disorder associated with an increased activity of EGFR-TK.

Herein throughout, the phrase "a disease or disorder associated with" an indicated condition (e.g., deregulated EGFR expression and/or activity), means that an onset and/or progression of the disease or disorder is associated with, or involves, the indicated condition.

Exemplary diseases and disorders that are associated with deregulated expression and/or activity of EGFR typically include proliferative diseases and disorders such as cancer.

As used herein, the terms "cancer" and "tumor" are interchangeably used. The terms refer to a malignant growth and/or tumor caused by abnormal and uncontrolled cell proliferation (cell division). The term "cancer" encompasses tumor metastases. The term "cancer cells" describes the cells forming the malignant growth or tumor.

Non-limiting examples of cancers and/or tumor metastases which can be identified and/or treated according to some embodiments of any of the embodiments described herein relating to cancer (including any of the aspects described herein) preferably include solid cancer and/or tumor metastasis, including, but not limiting to, tumors of the gastrointestinal tract (e.g., colon carcinoma, rectal carcinoma, colorectal carcinoma, colorectal cancer, colorectal adenoma, hereditary nonpolyposis type 1, hereditary nonpolyposis type 2, hereditary nonpolyposis type 3, hereditary nonpolyposis type 6; colorectal cancer, hereditary nonpolyposis type 7, small and/or large bowel carcinoma, esophageal carcinoma, tylosis with esophageal cancer, stomach carcinoma, pancreatic carcinoma, pancreatic endocrine tumors), endometrial carcinoma, dermatofibrosarcoma protuberans, gallbladder carcinoma, biliary tract tumors, prostate cancer, prostate adenocarcinoma, renal cancer (e.g., Wilms' tumor type 2 or type 1), liver cancer (e.g., hepatoblastoma, hepatocellular carcinoma, hepatocellular cancer), bladder cancer, embryonal rhabdomyosarcoma, germ cell tumor, trophoblastic tumor, testicular germ cells tumor, immature teratoma of ovary, uterine, epithelial ovarian, sacrococcygeal tumor, choriocarcinoma, placental site trophoblastic tumor, epithelial adult tumor, ovarian carcinoma, serous ovarian cancer, ovarian sex cord tumors, cervical carcinoma, uterine cervix carcinoma, small-cell and non-small cell lung carcinoma, nasopharyngeal, breast carcinoma (e.g., ductal breast cancer, invasive intraductal breast cancer, sporadic breast cancer, susceptibility to breast cancer, type 4 breast cancer, breast cancer-1, breast cancer-3, breast-ovarian cancer), squamous cell carcinoma (e.g., in head and neck), neurogenic tumor, astrocytoma, ganglioblastoma, neuroblastoma, lymphomas (e.g., Hodgkin's disease, non-Hodgkin's lymphoma, B-cell lymphoma, Diffuse large B-cell lymphoma (DLBCL), Burkitt lymphoma, cutaneous T-cell lymphoma, histiocytic lymphoma, lymphoblastic lymphoma, T-cell lymphoma, thymic lymphoma), gliomas, adenocarcinoma, adrenal tumor, hereditary adrenocortical carcinoma, brain malignancy (tumor), various other carcinomas (e.g., bronchogenic large cell, ductal, Ehrlich-Lettre ascites, epidermoid, large cell, Lewis lung, medullary, mucoepidermoid, oat cell, small cell, spindle cell, spinocellular, transitional cell, undifferentiated, carcinosarcoma, choriocarcinoma, cystadenocarcinoma), ependimoblastoma, epithelioma, fibrosarcoma, giant cell tumor, glial tumor, glioblastoma (e.g., multiforme, astrocytoma), glioma hepatoma, heterohybridoma, heteromyeloma, histiocytoma, hybridoma (e.g., B-cell), hypernephroma, insulinoma, islet tumor, keratoma, leiomyoblastoma, leiomyosarcoma, lymphosarcoma, mammary tumor, mastocytoma, medulloblastoma, mesothelioma, metastatic tumor, monocyte tumor, multiple myeloma, myelodysplastic syndrome, myeloma, nephroblastoma, nervous tissue glial tumor, nervous tissue neuronal tumor, neurinoma, neuroblastoma, oligodendroglioma, osteochondroma, osteomyeloma, osteosarcoma (e.g., Ewing's), papilloma, transitional cell, pheochromocytoma, pituitary tumor (invasive), plasmacytoma, retinoblastoma, rhabdomyosarcoma, sarcoma (e.g., Ewing's, histiocytic cell, Jensen, osteogenic, reticulum cell), schwannoma, subcutaneous tumor, teratocarcinoma (e.g., pluripotent), teratoma, testicular tumor, thymoma and trichoepithelioma, gastric cancer, fibrosarcoma, glioblastoma multiforme, multiple glomus tumors, Li-Fraumeni syndrome, liposarcoma, lynch cancer family syndrome II, male germ cell tumor, medullary thyroid, multiple meningioma, endocrine neoplasia myxosarcoma, paraganglioma, familial nonchromaffin, pilomatricoma, papillary, familial and sporadic, rhabdoid predisposition syndrome, familial, rhabdoid tumors, soft tissue sarcoma, and Turcot syndrome with glioblastoma.

In some embodiments, the proliferative disease or disorder is non-small cell lung cancer (NSCLC), pancreatic cancer, head and neck squamous cell carcinoma (HNSCC), brain cancer, breast cancer, esophageal cancer, gastric cancer, renal cancer, cervical cancer, ovarian cancer, hepatocellular cancer, malignant glioma, prostate cancer, colorectal cancer (CRC), bladder cancer, gynecological cancer, thyroid cancer and lymphoma.

In some embodiments, the proliferative disease or disorder is NSCLC.

A proliferative disease or disorder associated with deregulated expression and/or activity of EGFR can alternatively be a non-cancerous, or non-neoplastic, disease or disorder which involves uncontrolled and/or hyper-proliferation of cells. Non-cancerous hyper-proliferative diseases refer to diseases or disorders of which onset and/or progression is associated with non-malignant cell proliferation. Examples of such diseases and disorders include, but are not limited to atherosclerosis, rheumatoid arthritis, psoriasis, fibrosis, idiopathic pulmonary fibrosis, scleroderma and cirrhosis of the liver.

A radioimaging method according to some embodiments of the present invention is therefore for determining if the patient has a proliferative disease or disorder as described herein.

In some embodiments, the radioimaging is for determining if a patient has a disease or disorder associated with deregulated activity and/or expression of EGFR (e.g., a proliferative disease or disorder as described herein, such as cancer).

In some embodiments, the patient is suspected as having the disease or disorder as described herein. In some embodiments, the patient is diagnosed as having the disease or disorder and the radioimaging is for determining a distribution of the hyper-proliferating cells (e.g., cancer cells or tumors) in the patient's body, by determining a distribution of EGFR in the patient's body.

In some embodiments, the patient is diagnosed, or is suspected to be diagnosed, with cancer, and the radioimaging is for determining the location of primary and/or metastatic tumors (by determining the distribution of the radiolabeled compound in the patient's body or portion thereof).

In some of any of the embodiments described herein, the radioimaging is for monitoring or determining a mutational status of EGFR.

According to an aspect of some embodiments of the present invention there is provided a method of radioimaging, or a use of the radiolabeled compounds as described herein in radioimaging, or as radioimaging agents, as described herein, and the radioimaging is for determining a mutational status of EGFR in a patient.

In some of these embodiments, the patient is diagnosed (or is suspected to be diagnosed) with a disease or disorder associated with deregulated expression and/or activity of EGFR, as described herein, and determining a mutational status of EGFR is used for determining a suitable treatment for this patient.

In some of any of the embodiments described herein, a patient is diagnosed, or is suspected to be diagnosed, with the indicated disease or disorder, by means known in the art, such as, for example, imaging methods such as computed tomography, MRI, X-ray imaging, and/or by means of biopsy, determination of biomarkers in blood samples, etc.

Alternatively, a method of radioimaging as described herein is used for determining if the patient has a disease or disorder associated with deregulated expression and/or activity of EGFR, as described herein, and determining the mutational status of the disease or disorder is effected simultaneously with this diagnosis.

In some embodiments, a level and/or distribution of the radiolabeled compound in the patient's body or the portion thereof is indicative of a presence and/or distribution of a mutation variant of EGFR gene which confers sensitivity to an inhibitor of EGFR-TK.

In some embodiments, a mutation variant of EGFR gene which confers sensitivity to an inhibitor of EGFR-TK is a point mutation in exon 21 of the EGFR receptor (L858R), and/or exon 19 deletions such as the del(E746-A750).

Thus, an uptake of the compound by certain cells, tissues or organs is indicative of a presence of such a mutation variant, and is further indicative of its distribution.

In some embodiments, an absence of the compound in the patient's body or the portion thereof is indicative of a presence and/or distribution of a mutation variant of the EGFR gene which does not confers sensitivity to an inhibitor of EGFR-TK or which is resistant to an inhibitor of EGFR-TK, or of a non-mutated (wild-type) EGFR gene.

As described herein, deregulated expression and/or activity of EGFR can be associated with a mutated EGFR gene. There are various mutation variants of the EGFR gene, and each such variant leads to differently deregulated EGFR. Identifying the mutational status of EGFR is therefore highly desired for determining an efficient treatment of a patient.

In some embodiments, a mutational status of EGFR in a patient can be determined by the radioimaging method as described herein, by determining the uptake, distribution and pharmacokinetic parameters of the radiolabeled compound. Determining the pharmacokinetic parameters can be performed by methods known in the art, for example, as described in Petrulli et al., Neoplasia Vol. 15, No. 12, 2013; and Bahce et al., Clin Cancer Res; 19(1) Jan. 1, 2013, which are incorporated by reference as if fully set forth herein.

The radiolabeled compounds as described herein, by exhibiting high affinity towards EGFR-TK with increased TK activity, are therefore useful for determining if a patient has an activating mutation in the tyrosine kinase domain of an EGFR gene which confers sensitivity to an inhibitor of EGFR-TK (due to increased TK activity).

In some embodiments, the radioimaging is for monitoring or determining a presence (or absence) of an activating mutation in the tyrosine kinase domain of an EGFR gene which confers sensitivity to an inhibitor of EGFR-TK.

A high uptake of the radiolabeled compound by certain cells, tissues or organs (e.g., cancer cells) in the patient's body is indicative of a presence of such an activating mutation, whereby no uptake is indicative of an absence of such an activating mutation (and is indicative, for example, of the presence of deregulated EGFR of a wild-type EGFR gene or of deregulated EGFR of another mutations variant in the EGFR gene).

In exemplary embodiments, a method as described herein is used for determining a mutational status of a primary tumor and/or of tumor metastases.

As further discussed herein, by determining a mutational status of EGFR in a patient, a suitable therapy (e.g., first-line treatment) can be selected.

In some embodiments, based on a level and/or distribution and/or pharmacokinetic parameters of the radiolabeled compound, the EGFR mutation variant is determined and an EGFR-TKI inhibitor suitable for this particular mutation is determined as suitable for treating the patient.

For example, studies have shown that EGFR activated by TKD (tyrosine kinase domain) mutations in NSCLC can be inhibited by erlotinib and CI-1033 (canertinib) but not by lapatinib or HKI-272 (neratinib), whereas the same receptor activated by extracellular mutations in glioblastoma is conversely inhibited by lapatinib and HKI-272 (neratinib) but not by erlotinib or CI-1033 (canertinib). See, for example, Vivanco et al. (2012) Cancer Discovery 2, 458-471.

According to some of any of the embodiments described herein, the radioimaging is for determining if the patient has a disease or disorder treatable by an inhibitor of EGFR-TK.

According to some of any of the embodiments described herein, the radioimaging is for determining if the patient is responsive to a treatment with an inhibitor of EGFR-TK inhibitor.

An uptake of a radiolabeled compound as described herein at, for example, a tumor site, is indicative of an EGFR-TKI therapy as a suitable treatment approach for the patient. A distribution and corresponding levels of the radiolabeled compound are indicative of an uptake of the radiolabeled compound at a tumor site, be it a primary tumor or tumor metastases.

According to some of any of the embodiments described herein, the patient is diagnosed as having a disease or disorder associated with deregulated expression and/or activity, and the radioimaging is for determining if the patient should be treated with an EGFR-TK inhibitor or with another agent, as described herein.

In some embodiments, the inhibitor of EGFR-TK is erlotinib.

However, and based on the level and/or distribution of the radiolabeled compound, and/or the determined mutational status of EGFR, other EGFR-TK inhibitors can be selected as a suitable treatment of the patient, as described herein.

Any EGFR-TK inhibitor known in the art is contemplated herein, in any of the respective embodiments, including, but not limited to, afatinib, gefitinib (Iressa), lapatinib, and vandetanib.

According to an aspect of some embodiments of the present invention there is provided a method of radioimaging, or a use of the radiolabeled compounds as described herein in radioimaging, as described herein, and the radioimaging is for determining if a patient is responsive to a treatment with an inhibitor of EGFR-TK.

As discussed herein, a presence and/or accumulation (determined by determining a level and/or distribution; uptake) of the compound in the patient's body or a portion thereof is indicative of the patient being responsive to a treatment with an inhibitor of EGFR-TK.

In some embodiments, such a method is suitable for determining a first-line therapy for a patient who is diagnosed as having, or as suspected of having, a disease or disorder associated with deregulated expression and/or activity of EGFR, as described herein, for example, a proliferative disease or disorder as described herein, e.g., NSCLC.

In some embodiments, the level and/or distribution of the radiolabeled compound is indicative of a presence and/or distribution (biodistribution) of an activating mutation in the tyrosine kinase domain of the EGFR gene which confers sensitivity to the treatment, and hence of a patient being responsive to treatment with an inhibitor of EGFR-TK, as described herein.

In some of any of the embodiments described herein, the level and/or distribution and/or pharmacokinetic parameters of the radiolabeled compound in a patient's body or a portion thereof is indicative of a mutational status of the EGFR gene in the patient's body or a portion thereof, including wild-type and/or mutated EGFR gene, for which treatment with an inhibitor of EGFR-TK is useful.

In some embodiments, the radioimaging is performed following a treatment with EGFR-TK inhibitor, and is for determining an emergence of a resistance to the treatment with such an inhibitor.

In some embodiments, an absence of the radiolabeled compound in the patient's body or a portion thereof (no uptake of the compound in a patient's body or a portion thereof) (e.g., following a treatment with an inhibitor of EGFR-TK) is indicative of a presence of a mutation variant in the EGFR gene which confers insensitivity or resistance to a treatment with the EGFR-TKI.

In some of any of the embodiments described herein, a method of radioimaging as described herein in any of the respective embodiments, is useful in the course of treatment of a patient diagnosed with a disease or disorder associated with deregulated expression and/or activity of EGFR, as defined herein.

According to an aspect of some embodiments of the present invention there is provided a method of treating a patient diagnosed with a disease or disorder associated with deregulated expression and/or activity of EGFR, as defined herein.

According to some embodiments, such a treatment comprises:

administering the radiolabeled compound or the composition as described herein to the patient;

determining a level and/or distribution of the radiolabeled compound in the patient's body or the portion thereof by employing a nuclear imaging technique, the level and/or distribution being indicative of the patient's responsiveness to a treatment with an inhibitor of EGFR-TK, as described herein; and based on the determining, administering to the patient an inhibitor of EGFR-TK or an agent for regulating the expression and/or activity of EGFR other than an EGFR-TK inhibitor (e.g., a cytotoxic agent, as described herein).

In some of these embodiments, following the determining, the patient is identified as responsive to treatment with an inhibitor of EGFR-TK, as described herein, and is administered with the inhibitor of EGFR-TK.

Alternatively, the patient is indentified as non-responsive to EGFR-TK inhibitor therapy and is administered by another agent of choice.

In some embodiments, the patient is identified as responsive to treatment with an inhibitor of EGFR-TK, as described herein, and is administered with the inhibitor of EGFR-TK, and following a certain time period, referred to herein as first time period, the patient is subjected to another radioimaging method as described herein.

In some of these embodiments, the method further comprises, following the first time period, determining an emergence of a resistance to the inhibitor of EGFR-TK, by performing a radioimaging (a second radioimaging) as described herein. The second radioimaging is used for determining a presence or absence of a secondary mutation which accounts for emergence of resistance to the EGFR-TKI in the patient (e.g., acquired mutations in the EGFR gene) and/or of non-responsiveness to further treatment with EGFR-TK.

Based on the radioimaging, the patient is administered with the EGFR-TKI inhibitor for an additional (second) time period, if it is determined that such a secondary (acquired) mutation is absent, or is administered with another agent for regulating the expression and/or activity of EGFR for the second time period, namely, the treatment is replaced.

The radioimaging can be repeated following the second time period, and following additional time periods, as long as it is determined that the patient remains responsive to the EGFR-TK inhibitor treatment.

Such embodiments relate to a method of treating a disease or disorder associated with deregulated EGFR, while selecting a therapy of choice and while optionally longitudinally monitoring the treatment's efficiency, namely monitoring the patient's responsiveness to a treatment with an inhibitor of EGFR-TK (EGFR-TKI therapy).

In some of any of the embodiments described herein, the radioimaging further comprises administering to the patient a non-selective radioimaging agent, for example, a radioimaging agent that binds to any EGFR which features overexpression and/or overactivity, which can be expressed by a wild-type EGFR gene, or any mutation variant of the EGFR gene.

The level and/or distribution of the non-selective radioimaging agent provides information of the level and/or distribution of EGFR in the patient's body and/or a portion thereof, regardless of the mutational status of the EGFR, and is generally indicative of abnormal proliferation.

In some of the embodiments related to treatment of a patient, monitoring the responsiveness of a patient to EGFR-TKI therapy is used for determining or adjusting the dose and/or mode of administration of the EGFR-TK inhibitor.

By "dose" in the context of these embodiments, reference is made to "a therapeutically effective amount", as defined herein. In some embodiments, by "dose" it is meant the total amount of a drug (e.g., EGFR-TKI) administered per a treatment period. Increasing the dose can be made by increasing the amount of a drug per administration, increasing the total number of administrations during a treatment period and/or lowering the intervals between administrations.

In some embodiments, using a method of treatment as described herein, the radioimaging performed following the first time period can provide information on the treatment efficacy, and can be used for determining the therapy of choice in the second treatment period.

For example, in cases where in the radioimaging performed following the first time period, it is observed that the uptake (level and/or distribution) of the radiolabeled compound remained unchanged compared to the uptake of the radiolabeled compound before the first treatment period, the uptake is indicative of a tumor that maintains its sensitivity to EGFR-TKIs, yet the dose should be increased and/or the mode of administration replaced, in order to eliminate the tumor.

In such embodiments, the patient is administered with the EGFR-TKI inhibitor for an additional (second) time period, yet the EGFR-TKI is administered at a dose higher than the dose during the first time period, as described herein, and/or at a different mode of administration. Optionally, a different RGFR-TKI can be administered.

In another example, in cases where in the radioimaging performed following the first treatment it is observed that there is an uptake (level and/or distribution) of the radiolabeled compound but the uptake regions are smaller and/or some uptake regions are diminished, compared to the uptake of the radiolabeled compound before the first treatment period, the uptake is indicative of a tumor that maintains its sensitivity to EGFR-TKIs, that is responsive to the treatment and is eliminated by the treatment. This can be verified by performing radioimaging with a non-selective radioimaging agent as described herein, as well as with other imaging modalities, such as CT, so as to rule out the appearance of tumors with secondary mutations in the EGFR gene.

The treatment is therefore continued at the same and optionally at lower-doses, for the second time period.

In another example, in cases where in the radioimaging performed following the first treatment it is observed that there is reduced or no uptake (level and/or distribution) of the radiolabeled compound, yet radioimaging with a non-selective radioimaging agent or with an alternative imaging modality shows that the tumor remained unchanged during first treatment period, the (lack of) uptake is most likely indicative of the presence of secondary mutations in the EGFR gene that confer resistance to EGFR-TKI. In such cases, the therapy is replaced.

The treatment described herein therefore provides immediate indication of the treatment efficacy, and hence immediate personalized adjustment of the therapy during treatment.

The treatment described herein further enables to gain a comprehensive information of the mutational status of the EGFR gene and its respective distribution within the patient's body. Thus, for example, it enables to detect tumors with varying mutations, for example, in cases where a primary tumor is a result of wild-type EGFR gene and its metastases feature activating mutations in the tyrosine kinase domain of the EGFR gene, and vice versa, or in cases where a primary tumor features activating mutations in the tyrosine kinase domain of the EGFR gene, and some or all of its metastases feature secondary mutations which are resistant to EGFR-TKI therapy, and vice versa. This further allows to immediately respond to the disease's progression by adjusting the therapy accordingly.

In some of any of the embodiments described herein, in addition to the radioimaging, other diagnosis measures are applied, such as biopsy, as complementary measures for verifying, supporting, and/or providing further information on top of, the radioimaging findings.

In some of any of the embodiments described herein for radioimaging, the radioimaging further comprises, prior to administering the radiolabeled compound to a patient, preparing the radiolabeled compound.

In some of these embodiments, the radiolabeled compound is prepared as described herein in any of the respective embodiments and any combination thereof.

In some of these embodiments, the radiolabeled is prepared 1, 2, 3 or even more hours before being administered to the patient, depending on the radioactive halogen used (and its half life), and as described hereinabove.

Radiotherapy:

According to an aspect of some embodiments of the present invention, there is provided a radiolabeled compound as described herein for use in radiotherapy in a patient in need thereof.

According to an aspect of some embodiments of the present invention, there is provided a use of a radiolabeled compound as described herein in the manufacture of a medicament for radiotherapy (in the manufacture of a radiotherapeutic agent).

According to an aspect of some embodiments of the present invention, there is provided a method of radiotherapy, which comprises administering a radiolabeled compound as described herein to a patient in need thereof.

The radiotherapy described herein is suitable for patients diagnosed with deregulated expression and/or activity of EGFR, as described herein, e.g., a proliferative disease or disorder.

In some embodiments, the radiotherapy is for treating a patient diagnosed as having an activating mutation in the tyrosine kinase domain of EGFR which confers sensitivity to an inhibitor of EGFR-TK. The patient can be diagnosed using a radioimaging as described herein in any of the respective embodiments, or by any other method known in the art.

In some embodiments, the patient is diagnosed as having a disease or disorder that is treatable by (responsive to) an inhibitor of EGFR-TK.

The bromine-77, iodine-124 and iodine-131 radiolabeled compounds herein described can be used to effect a radiotherapy as described herein by administering to a patient in need thereof a therapeutically effective amount of a radiolabeled compound as described herein, mixed with, for example, a pharmaceutically acceptable carrier.

For any compound used in the method of the invention, a therapeutically effective amount, also referred to herein as a therapeutically effective dose, can be estimated initially from cell culture assays. For example, a dose can be formulated in animal models to achieve a circulating concentration range that includes the $IC_{50}$ or the $IC_{100}$ as determined in cell culture. Such information can be used to more accurately determine useful doses in humans. Initial dosages can also be estimated from in vivo data. Using these initial guidelines one having ordinary skill in the art could determine an effective dosage in humans.

Moreover, toxicity and therapeutic efficacy of the radiolabeled compounds described herein can be determined by standard pharmaceutical procedures in cell cultures or experimental animals, e.g., by determining the $LD_{50}$ and the $ED_{50}$. The dose ratio between toxic and therapeutic effect is the therapeutic index and can be expressed as the ratio between $LD_{50}$ and $ED_{50}$. Compounds which exhibit high therapeutic indices are preferred. The data obtained from these cell cultures assays and animal studies can be used in formulating a dosage range that is not toxic for use in human. The dosage of such compounds lies preferably within a range of circulating concentrations that include the EDso with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: The Pharmacological Basis of Therapeutics, chapter 1, page 1).

Dosage amount and interval may be adjusted individually to provide plasma levels of the active compound which are sufficient to maintain therapeutic effect. Usual patient dosages for oral administration range from about 50-2000 mg/kg/day, commonly from about 100-1000 mg/kg/day, preferably from about 150-700 mg/kg/day and most preferably from about 250-500 mg/kg/day. Preferably, therapeutically effective serum levels will be achieved by administering multiple doses each day. In cases of local administration or selective uptake, the effective local concentration of the drug may not be related to plasma concentration. One having skill in the art will be able to optimize therapeutically effective local dosages without undue experimentation.

The radiolabeled compound utilized in the methods of radiotherapy described herein can be used in combination with one or more other agents suitable for treating the disease or disorder, for example, cytotoxic agents, or any other anti-cancer agents known in the art.

In some of any of the embodiments described herein for radiotherapy, the radiotherapy further comprises, prior to administering the radiolabeled compound to a patient, preparing the radiolabeled compound.

In some of these embodiments, the radiolabeled compound is prepared as described herein in any of the respective embodiments and any combination thereof.

In some of these embodiments, the radiolabeled compound is prepared several hours, for example, 24 hours or even several days (e.g., 2 or more days) before being administered to the patient, depending on the radioactive halogen used, and as described hereinabove.

Pharmaceutical Compositions:

Any of the radiolabeled compounds described herein can be formulated into a pharmaceutical composition which can be used for radiotherapy of a disease or for imaging, as described herein in any of the methods and uses and respective embodiments thereof. Such a composition includes as an active ingredient any of the radiolabeled compounds described herein and a pharmaceutically acceptable carrier.

As used herein a "pharmaceutical composition" refers to a preparation of one or more of the radiolabeled compounds described herein, with other chemical components such as pharmaceutically suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition.

Suitable routes of administration may, for example, include intravenous, intraperitoneal, intranasal, or intraocular injections, oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, or into the common coronary artery.

Alternately, one may administer the pharmaceutical composition in a local rather than systemic manner, for example, via injection of the pharmaceutical composition directly into a tissue region of a patient.

The term "tissue" refers to part of an organism consisting of cells designed to perform a function or functions. Examples include, but are not limited to, pulmonary tissue, pancreatic tissue, brain tissue, retina, skin tissue, hepatic tissue, breast tissue, bone, cartilage, connective tissue, blood tissue, muscle tissue, cardiac tissue, vascular tissue, renal tissue, gonadal tissue, rectal tissue, and hematopoietic tissue.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the active compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran.

Optionally, the suspension may also contain suitable stabilizers or agents which increase the solubility of the active ingredients to allow for the preparation of highly concentrated solutions.

The pharmaceutical composition of some embodiments of the invention may also be formulated in rectal compositions such as suppositories or retention enemas, using, e.g., conventional suppository bases such as cocoa butter or other glycerides.

In some embodiments, a pharmaceutical composition as described herein is prepared prior to administration to a patient.

In some embodiments, a pharmaceutical composition as described herein comprises a fluorine-18 radiolabeled compound as described herein, and is prepared 20-240 minutes, or 30 to 240 minutes, or 30 to 180 minutes, or 30 to 120 minutes, or 30 to 60 minutes, prior to administration to a patient.

In some embodiments, a pharmaceutical composition as described herein comprises a bromine-76 or bromine-77 radiolabeled compound as described herein, and can be prepared 1-48 hours, or 1-24 hours minutes, prior to administration to a patient, although shorter time periods are also contemplated.

In some embodiments, a pharmaceutical composition as described herein comprises iodine-123, iodine-124 or iodine-125 radiolabeled compound as described herein, and can be prepared from 1 hour to several days, prior to administration to a patient, as described herein, although shorter time periods are also contemplated.

In some of any of the embodiments described herein, a radioimaging method as described herein is performed 0-120 minutes, or 0-60 minutes, or 0-40 minutes, or 0-20 minutes, after administration of the composition to a patient.

It is expected that during the life of a patent maturing from this application many relevant EGFR-TK inhibitors will be developed and the scope of the term "inhibitor of EGFR-TK" is intended to include all such new technologies a priori.

It is further expected that during the life of a patent maturing from this application many relevant mutations variants in the EGFR gene will be uncovered and the scope of the term "mutation variant in the EGFR gene", including the scope of the term "activating mutation in the tyrosine kinase domain of an EGFR gene" is intended to include all such mutation variants a priori.

It is further expected that during the life of a patent maturing from this application relevant radioactive halogens and respective nuclear imaging techniques will be developed and the scope of the term "radioactive halogen" is intended to include all such new technologies a priori.

As used herein the term "about" refers to ±10% or ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

For any of the embodiments described herein, and any combination thereof, the compound may be in a form of a salt, for example, a pharmaceutically acceptable salt.

As used herein, the phrase "pharmaceutically acceptable salt" refers to a charged species of the parent compound and its counter-ion, which is typically used to modify the solubility characteristics of the parent compound and/or to reduce any significant irritation to an organism by the parent compound, while not abrogating the biological activity and properties of the administered compound. A pharmaceutically acceptable salt of a compound as described herein can alternatively be formed during the synthesis of the compound, e.g., in the course of isolating the compound from a reaction mixture or re-crystallizing the compound.

In the context of some of the present embodiments, a pharmaceutically acceptable salt of the compounds described herein may optionally be an acid addition salt comprising at least one basic (e.g., amine and/or guanidine) group of the compound which is in a positively charged form (e.g., wherein the basic group is protonated), in combination with at least one counter-ion, derived from the selected base, that forms a pharmaceutically acceptable salt.

The acid addition salts of the compounds described herein may therefore be complexes formed between one or more basic groups of the compound and one or more equivalents of an acid.

Depending on the stoichiometric proportions between the charged group(s) in the compound and the counter-ion in the salt, the acid additions salts can be either mono-addition salts or poly-addition salts.

The phrase "mono-addition salt", as used herein, refers to a salt in which the stoichiometric ratio between the counter-ion and charged form of the compound is 1:1, such that the addition salt includes one molar equivalent of the counter-ion per one molar equivalent of the compound.

The phrase "poly-addition salt", as used herein, refers to a salt in which the stoichiometric ratio between the counter-ion and the charged form of the compound is greater than 1:1 and is, for example, 2:1, 3:1, 4:1 and so on, such that the addition salt includes two or more molar equivalents of the counter-ion per one molar equivalent of the compound.

An example, without limitation, of a pharmaceutically acceptable salt would be an ammonium cation or guanidinium cation and an acid addition salt thereof.

The acid addition salts may include a variety of organic and inorganic acids, such as, but not limited to, hydrochloric acid which affords a hydrochloric acid addition salt, hydrobromic acid which affords a hydrobromic acid addition salt, acetic acid which affords an acetic acid addition salt, ascorbic acid which affords an ascorbic acid addition salt, benzenesulfonic acid which affords a besylate addition salt, camphorsulfonic acid which affords a camphorsulfonic acid addition salt, citric acid which affords a citric acid addition salt, maleic acid which affords a maleic acid addition salt, malic acid which affords a malic acid addition salt, methanesulfonic acid which affords a methanesulfonic acid (mesylate) addition salt, naphthalenesulfonic acid which affords a naphthalenesulfonic acid addition salt, oxalic acid which affords an oxalic acid addition salt, phosphoric acid which affords a phosphoric acid addition salt, toluenesulfonic acid which affords a p-toluenesulfonic acid addition salt, succinic acid which affords a succinic acid addition salt, sulfuric acid which affords a sulfuric acid addition salt, tartaric acid which affords a tartaric acid addition salt and trifluoroacetic acid which affords a trifluoroacetic acid addition salt. Each of these acid addition salts can be either a mono-addition salt or a poly-addition salt, as these terms are defined herein.

The present embodiments further encompass any enantiomers, diastereomers, prodrugs, solvates, hydrates and/or pharmaceutically acceptable salts of the compounds described herein.

As used herein, the term "enantiomer" refers to a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems. In the context of the present embodiments, a compound may exhibit one or more chiral centers, each of which exhibiting an R- or an S-configuration and any combination, and compounds according to some embodiments of the present invention, can have any their chiral centers exhibit an R- or an S-configuration.

The term "diastereomers", as used herein, refers to stereoisomers that are not enantiomers to one another. Diastereomerism occurs when two or more stereoisomers of a compound have different configurations at one or more, but not all of the equivalent (related) stereocenters and are not mirror images of each other. When two diastereoisomers differ from each other at only one stereocenter they are epimers. Each stereo-center (chiral center) gives rise to two different configurations and thus to two different stereoisomers. In the context of the present invention, embodiments of the present invention encompass compounds with multiple chiral centers that occur in any combination of stereo-configuration, namely any diastereomer.

The term "prodrug" refers to an agent, which is converted into the active compound (the active parent drug) in vivo. Prodrugs are typically useful for facilitating the administration of the parent drug. They may, for instance, be bioavailable by oral administration whereas the parent drug is not. A prodrug may also have improved solubility as compared with the parent drug in pharmaceutical compositions. Prodrugs are also often used to achieve a sustained release of the active compound in vivo. An example, without limitation, of a prodrug would be a compound of the present invention, having one or more carboxylic acid moieties, which is administered as an ester (the "prodrug"). Such a prodrug is hydrolyzed in vivo, to thereby provide the free compound (the parent drug). The selected ester may affect both the solubility characteristics and the hydrolysis rate of the prodrug.

The term "solvate" refers to a complex of variable stoichiometry (e.g., di-, tri-, tetra-, penta-, hexa-, and so on), which is formed by a solute (the compound of the present invention) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

The terms "hydroxyl" or "hydroxy", as used herein, refer to an —OH group.

As used herein, the term "amine" describes a —NR'R" group where each of R' and R" is independently hydrogen, alkyl, alkenyl, alkynyl, cycloalkyl, heteroalicyclic, aryl, heteroaryl, alkaryl, alkheteroaryl, or acyl, as these terms are defined herein. Alternatively, one or both of R' and R" can be, for example, hydroxy, alkoxy, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, C-carboxylate, O-carboxylate, N-thiocarbamate, O-thiocarbamate, urea, thiourea, N-carbamate, O-carbamate, C-amide, N-amide, guanyl, guanidine and hydrazine.

The term "amide" also describes a —NR'— linking group (a biradical group, attached to two moieties), with R' as described herein.

As used herein, the term "alkyl" describes an aliphatic hydrocarbon including straight chain and branched chain groups. The alkyl may have 1 to 20 carbon atoms, or 1-10 carbon atoms, and may be branched or unbranched. Whenever a numerical range; e.g., "1-10", is stated herein, it implies that the group, in this case the alkyl group, may contain 1 carbon atom, 2 carbon atoms, 3 carbon atoms, etc., up to and including 10 carbon atoms. In some embodiments, the alkyl is a lower alkyl, including 1-6 or 1-4 carbon atoms.

An alkyl can be substituted or unsubstituted. When substituted, the substituent can be, for example, one or more of an alkyl (forming a branched alkyl), an alkenyl, an alkynyl, a cycloalkyl, an aryl, a heteroaryl, a heteroalicyclic, a halo, a trihaloalkyl, a hydroxy, an alkoxy and a hydroxyalkyl as these terms are defined hereinbelow. An alkyl substituted by aryl is also referred to herein as "alkaryl", an example of which is benzyl. The alkyl can be substituted by other substituents, as described hereinbelow.

The term "alkenyl" describes an unsaturated alkyl, as defined herein, having at least two carbon atoms and at least one carbon-carbon double bond, e.g., allyl, vinyl, 3-butenyl, 2-butenyl, 2-hexenyl and i-propenyl. The alkenyl may be substituted or unsubstituted by one or more substituents, as described hereinabove.

The term "alkynyl", as defined herein, is an unsaturated alkyl having at least two carbon atoms and at least one carbon-carbon triple bond. The alkynyl may be substituted or unsubstituted by one or more substituents, as described hereinabove.

The term "cycloalkyl" refers to an all-carbon monocyclic or fused ring (i.e., rings which share an adjacent pair of carbon atoms), branched or unbranched group containing 3 or more carbon atoms where one or more of the rings does not have a completely conjugated pi-electron system, and may further be substituted or unsubstituted. Exemplary cycloalkyl groups include, for example, cyclopropyl, cyclobutyl, cyclopentyl, cyclohexyl, or cyclododecyl. The cycloalkyl can be substituted or unsubstituted.

The term "aryl" describes an all-carbon monocyclic or fused-ring polycyclic (i.e., rings which share adjacent pairs of carbon atoms) groups having a completely conjugated pi-electron system. The aryl group may be unsubstituted or substituted by one or more substituents. An aryl substituted by alkyl is also referred to herein as "aralkyl", as example of which is toluyl.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. Representative examples are thiadiazole, pyridine, pyrrole, oxazole, indole, purine and the like. The heteroaryl group may be unsubstituted or substituted by one or more substituents.

The term "heteroalicyclic", as used herein, describes a monocyclic or fused ring group having in the ring(s) one or more atoms such as nitrogen, oxygen and sulfur. The rings may also have one or more double bonds. However, the rings do not have a completely conjugated pi-electron system. Representative examples are morpholine, piperidine, piperazine, tetrahydrofurane, tetrahydropyrane and the like. The heteroalicyclic may be substituted or unsubstituted.

The term "halide", as used herein, refers to the anion of a halo atom, i.e. F$^-$, Cl$^-$, Br$^-$ and I$^-$.

The term "halo" or "halogen" refers to F, Cl, Br and I atoms as substituents.

The term "alkoxide" refers to an R'—O$^-$ anion, wherein R' is as defined hereinabove.

The term "alkoxy" refers to an —OR' group, wherein R' is alkyl or cycloalkyl, as defined herein.

The term "aryloxy" refers to an —OR' group, wherein R' is aryl, as defined herein.

The term "heteroaryloxy" refers to an —OR' group, wherein R' is heteroaryl, as defined herein.

The term "thioalkoxy" refers to an —SR' group, wherein R' is alkyl or cycloalkyl, as defined herein.

The term "thioaryloxy" refers to an —SR' group, wherein R' is aryl, as defined herein.

The term "thioheteroaryloxy" refers to an —SR' group, wherein R' is heteroaryl, as defined herein.

The term "hydroxyalkyl," as used herein, refers to an alkyl group, as defined herein, substituted with one or more hydroxy group(s), e.g., hydroxymethyl, 2-hydroxyethyl and 4-hydroxypentyl.

The term "aminoalkyl," as used herein, refers to an alkyl group, as defined herein, substituted with one or more amino group(s).

The term "alkoxyalkyl," as used herein, refers to an alkyl group substituted with one or more alkoxy group(s), e.g., methoxymethyl, 2-methoxyethyl, 4-ethoxybutyl, n-propoxyethyl and t-butylethyl.

The term "trihaloalkyl" refers to —CX$_3$, wherein X is halo, as defined herein. An exemplary haloalkyl is CF$_3$.

A "guanidine" or "guanidine" or "guanidinyl" or "guanidyl" group refers to an —RaNC(=NRd)-NRbRc group, where each of Ra, Rb, Rc and Rd can each be as defined herein for R' and R".

A "guanyl" or "guanine" group refers to an RaRbNC(=NRd)- group, where Ra, Rb and Rd are each as defined herein for R' and R".

Whenever an alkyl, cycloalkyl, aryl, alkaryl, heteroaryl, heteroalicyclic, acyl and any other moiety or group as described herein is substituted, it includes one or more substituents, each can independently be, but are not limited to, hydroxy, alkoxy, thiohydroxy, thioalkoxy, aryloxy, thioaryloxy, alkaryl, alkyl, alkenyl, alkynyl, sulfonate, sulfoxide, thiosulfate, sulfate, sulfite, thiosulfite, phosphonate, cyano, nitro, azo, sulfonamide, carbonyl, thiocarbonyl, C-carboxylate, O-carboxylate, N-thiocarbamate, O-thiocarbamate, oxo, thiooxo, oxime, acyl, acyl halide, azo, azide, urea, thiourea, N-carbamate, O-carbamate, C-amide, N-amide, guanyl, guanidyl, hydrazine and hydrazide, as these terms are defined herein.

The term "cyano" describes a —C≡N group.

The term "nitro" describes an —NO$_2$ group.

The term "sulfate" describes a —O—S(=O)$_2$—OR' end group, as this term is defined hereinabove, or an —O—S(=O)$_2$—O— linking group, as these phrases are defined hereinabove, where R' is as defined hereinabove.

The term "thiosulfate" describes a —O—S(=S)(=O)—OR' end group or a —O—S(=S)(=O)—O— linking group, as these phrases are defined hereinabove, where R' is as defined hereinabove.

The term "sulfite" describes an —O—S(=O)—O—R' end group or a —O—S(=O)—O— group linking group, as these phrases are defined hereinabove, where R' is as defined hereinabove.

The term "thiosulfite" describes a —O—S(=S)—O—R' end group or an —O—S(=S)—O— group linking group, as these phrases are defined hereinabove, where R' is as defined hereinabove.

The term "sulfinate" describes a —S(=O)—OR' end group or an —S(=O)—O— group linking group, as these phrases are defined hereinabove, where R' is as defined hereinabove.

The term "sulfoxide" or "sulfinyl" describes a —S(=O)R' end group or an —S(=O)— linking group, as these phrases are defined hereinabove, where R' is as defined hereinabove.

The term "sulfonate" or "sulfonyl" describes a —S(=O)$_2$—R' end group or an —S(=O)$_2$— linking group, as these phrases are defined hereinabove, where R' is as defined herein.

The term "S-sulfonamide" describes a —S(=O)$_2$—NR'R" end group or a —S(=O)$_2$—NR'— linking group, as these phrases are defined hereinabove, with R' and R" as defined herein.

The term "N-sulfonamide" describes an R'S(=O)$_2$—NR"— end group or a —S(=O)$_2$—NR'— linking group, as these phrases are defined hereinabove, where R' and R" are as defined herein.

The term "carbonyl" or "carbonate" as used herein, describes a —C(=O)—R' end group or a —C(=O)— linking group, as these phrases are defined hereinabove, with R' as defined herein.

The term "thiocarbonyl" as used herein, describes a —C(=S)—R' end group or a —C(=S)— linking group, as these phrases are defined hereinabove, with R' as defined herein.

The term "oxo" as used herein, describes a (=O) group, wherein an oxygen atom is linked by a double bond to the atom (e.g., carbon atom) at the indicated position.

The term "thiooxo" as used herein, describes a (=S) group, wherein a sulfur atom is linked by a double bond to the atom (e.g., carbon atom) at the indicated position.

The term "oxime" describes a =N—OH end group or a =N—O— linking group, as these phrases are defined hereinabove.

The term "acyl halide" describes a —(C=O)R"" group wherein R"" is halo, as defined hereinabove.

The term "azo" or "diazo" describes an —N=NR' end group or an —N=N— linking group, as these phrases are defined hereinabove, with R' as defined hereinabove.

The term "azide" describes an —N$_3$ end group.

The term "carboxylate" as used herein encompasses C-carboxylate and O-carboxylate.

The term "C-carboxylate" describes a —C(=O)—OR' end group or a —C(=O)—O— linking group, as these phrases are defined hereinabove, where R' is as defined herein.

The term "O-carboxylate" describes a —OC(=O)R' end group or a —OC(=O)— linking group, as these phrases are defined hereinabove, where R' is as defined herein.

A carboxylate can be linear or cyclic. When cyclic, R' and the carbon atom are linked together to form a ring, in C-carboxylate, and this group is also referred to as lactone. Alternatively, R' and O are linked together to form a ring in O-carboxylate. Cyclic carboxylates can function as a linking group, for example, when an atom in the formed ring is linked to another group.

The term "thiocarboxylate" as used herein encompasses C-thiocarboxylate and O-thiocarboxylate.

The term "C-thiocarboxylate" describes a —C(=S)—OR' end group or a —C(=S)—O— linking group, as these phrases are defined hereinabove, where R' is as defined herein.

The term "O-thiocarboxylate" describes a —OC(=S)R' end group or a —OC(=S)— linking group, as these phrases are defined hereinabove, where R' is as defined herein.

A thiocarboxylate can be linear or cyclic. When cyclic, R' and the carbon atom are linked together to form a ring, in C-thiocarboxylate, and this group is also referred to as thiolactone. Alternatively, R' and O are linked together to form a ring in O-thiocarboxylate. Cyclic thiocarboxylates can function as a linking group, for example, when an atom in the formed ring is linked to another group.

The term "carbamate" as used herein encompasses N-carbamate and O-carbamate.

The term "N-carbamate" describes an R"OC(=O)—NR'— end group or a —OC(=O)—NR'— linking group, as these phrases are defined hereinabove, with R' and R" as defined herein.

The term "O-carbamate" describes an —OC(=O)—NR'R" end group or an —OC(=O)—NR'— linking group, as these phrases are defined hereinabove, with R' and R" as defined herein.

A carbamate can be linear or cyclic. When cyclic, R' and the carbon atom are linked together to form a ring, in O-carbamate. Alternatively, R' and O are linked together to form a ring in N-carbamate. Cyclic carbamates can function as a linking group, for example, when an atom in the formed ring is linked to another group.

The term "carbamate" as used herein encompasses N-carbamate and O-carbamate.

The term "thiocarbamate" as used herein encompasses N-thiocarbamate and O-thiocarbamate. The term "O-thiocarbamate" describes a —OC(=S)—NR'R" end group or a —OC(=S)—NR'— linking group, as these phrases are defined hereinabove, with R' and R" as defined herein.

The term "N-thiocarbamate" describes an R"OC(=S)NR'— end group or a —OC(=S)NR'— linking group, as these phrases are defined hereinabove, with R' and R" as defined herein.

Thiocarbamates can be linear or cyclic, as described herein for carbamates.

The term "dithiocarbamate" as used herein encompasses S-dithiocarbamate and N-dithiocarbamate.

The term "S-dithiocarbamate" describes a —SC(=S)—NR'R" end group or a —SC(=S)NR'— linking group, as these phrases are defined hereinabove, with R' and R" as defined herein.

The term "N-dithiocarbamate" describes an R"SC(=S)NR'— end group or a —SC(=S)NR'— linking group, as these phrases are defined hereinabove, with R' and R" as defined herein.

The term "urea", which is also referred to herein as "ureido", describes a —NR'C(=O)—NR"R'" end group or a —NR'C(=O)—NR"— linking group, as these phrases are defined hereinabove, where R' and R" are as defined herein and R'" is as defined herein for R' and R".

The term "thiourea", which is also referred to herein as "thioureido", describes a —NR'—C(=S)—NR"R'" end group or a —NR'—C(=S)—NR"— linking group, with R', R" and R'" as defined herein.

The term "amide" as used herein encompasses C-amide and N-amide.

The term "C-amide" describes a —C(=O)—NR'R" end group or a —C(=O)—NR'— linking group, as these phrases are defined hereinabove, where R' and R" are as defined herein.

The term "N-amide" describes a R'C(=O)—NR"— end group or a R'C(=O)—N— linking group, as these phrases are defined hereinabove, where R' and R" are as defined herein.

The term "hydrazine" describes a —NR'—NR"R'"— end group or a —NR'—NR"— linking group, as these phrases are defined hereinabove, with R', R", and R'" as defined herein.

As used herein, the term "hydrazide" describes a —C(=O)—NR'—NR"R'" end group or a —C(=O)—NR'—NR"— linking group, as these phrases are defined hereinabove, where R', R" and R'" are as defined herein.

As used herein, the term "thiohydrazide" describes a —C(=S)—NR'—NR"R'" end group or a —C(=S)—

NR'—NR"— linking group, as these phrases are defined hereinabove, where R', R" and R''' are as defined herein.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Example 1

Chemical and Radio-Syntheses

Materials and Experimental Methods:

6-O-desmethylerlotinib (OSI 420) and 7-O-desmethylerlotinib (OSI 413) are obtainable from commercial vendors (e.g., Selleck Chemicals).

Fluoroethyltosylate, 1,2-Bis(tosyloxy)ethane and kyptofix K2.2.2 were obtained from ABX, Radeberg, Germany.

N,N-Dimethylformamide, Sodium hydride and Potassium carbonate were purchased from sigma Aldrich (Rehovot, Israel).

Acetonitrile and ethanol were purchased from Merck (Darmstadt, Germany).

Radioactive halides are generated as follows: Radioactive fluoride-18 ion is produced via the $^{18}O(p,n)^{18}F$ nuclear reaction using a IBA cyclotron equipped with a fluorine-18 target. The [$^{18}F$]fluoride is delivered from the cyclotron (in a 3 ml bolus of [$^{18}O$]H$_2$O) and trapped on a anion exchange cartridge to remove [$^{18}O$]H$_2$O. [$^{18}F$]Fluoride is then eluted into the reaction vessel using aqueous potassium carbonate (4 mg in 0.5 mL of water). A solution of kryptofix-2.2.2 (15 mg in 1 mL of acetonitrile) is then added to the reaction vessel and the [$^{18}F$] fluoride is dried by evaporating the water=acetonitrile azeotrope under heating and reduced pressure followed by cooling to 60° C.

Radioactive iodine-123, radioactive iodine-124 and radioactive iodine-131 are obtainable from commercial vendors.

Radioactive bromine-76 and radioactive bromine-77 are obtainable from commercial vendors.

Radiochemical purity is determined using an analytical HPLC Varian ProStar model 230 (Palo Alto, Calif., USA) equipped with UV Detector, JASCO UV-2075 plus (Tokyo, Japan) and PMT/scintillator detector Bioscan flow count).

Preparative HPLC is performed using a Varian 9012Q HPLC system employed with an Varian 9050 UV-VIS detector and C18 HPLC column (Bischoff Nucleosil C18, 7 μm, 250 mm×16 mm, Marchery-Nagel GmbH, Duren, Germany).

Semi-preparative HPLC is performed using Varian 9012Q HPLC system employed with a Varian 9050 UV-VIS detector and C18 column (Luna, Phenomenex, Torrance, Calif., USA).

Analytical HPLC is performed using analytical HPLC Varian ProStar model 230 (Palo Alto, Calif., USA) equipped with UV Detector, JASCO UV-2075 plus (Tokyo, Japan).

$^1$H-NMR and $^{19}$F-NMR spectra are obtained using Varian VXR-300 (300 MHz spectrometer equipped with a 5 mm probe).

HRMS was performed using an ESI LTQ Orbitrap XL spectrophotometer equipped with FTMS Analyzer (Resolution: 100000). The data collected using Xcalibur 2.1 program.

Synthesis of 6/7-haloalkylerlotinib—General Procedures:

Exemplary strategies for introducing a radiolabeled halogen (e.g., Fluorine-18; $F^{18}$) to erlotinib or a derivative thereof, according to some of the present embodiments, are based on introducing the radioactive halogen or the radioactive halogen-containing moiety to the terminal methyl of the methoxyethoxy substituent at position 6 or 7 of the quinazoline ring. These positions are readily available, synthesis-wise, for radiolabeling, and further, introduce a modification at a distal position with respect to the sites of the molecule that interact with the ATP-binding pocket of the EGFR-TK, thus maintaining (not interfering with) the binding affinity of erlotinib to EGFR-TK.

Several exemplary general strategies have been designed for introducing a halogen atom or a halogen-containing moiety at the indicated positions of erlotinib, as follows:

Exemplary general procedure I involves replacing the terminal methyl group of the methoxyethoxy moiety at position 6 or 7 of the quinazoline ring of erlotinib (or a derivative thereof) by a halomethyl (e.g., fluoromethyl, CH$_2$F; or, alternatively, CH$_2$X, with X being Br or I).

Exemplary general procedure II involves replacing the terminal methyl group of the methoxyethoxy moiety at position 6 or 7 of the quinazoline ring of erlotinib (or a derivative thereof) by a haloalkyl other than halomethyl (e.g., fluoroethyl, CH$_2$CH$_2$F; or (CH$_2$)qF or, alternatively, (CH$_2$)qX, with X as defined herein, wherein m is integer greater than 1).

In both general procedures I and II, a desmethyl derivative of erlotinib (or a derivative thereof), for example the commercially available 6-desmethylerlotinib (6-O-desmethyl erlotinib) or 7-desmethylerlotinib (7-O-desmethyl erlotinib), can be used as a starting material, although other starting materials are also contemplated.

The synthesis is effected as a one-step reaction, wherein the CH$_2$X (e.g., CH$_2$F) or (CH$_2$)qX (e.g., CH$_2$CH$_2$F) group is reacted with 6/7-desmethylerlotinib in one chemical step, using commercially available reagents, as exemplified in Schemes 1 and 2 below.

In brief, a 6/7-desmethylerlotinib or a 6/7-desmethyl erlotinib derivative is reacted with a fluorinated reagent as depicted in Schemes 1 and 2 in a polar solvent (e.g., DMF), in the presence of a base, optionally while heating to a temperature that ranges from about 40° C. to about 100° C. The reaction mixture is thereafter cooled, ethanol and ice are added, and the obtained mixture is filtered, concentrated and purified (e.g., by preparative HPLC).

Scheme 1

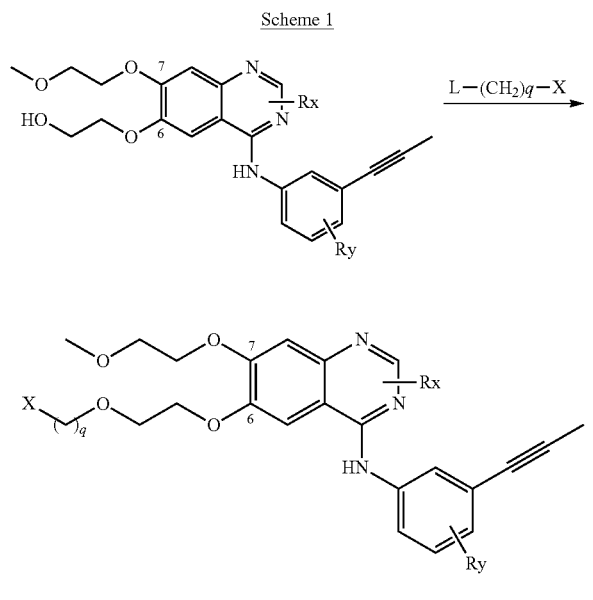

Scheme 2

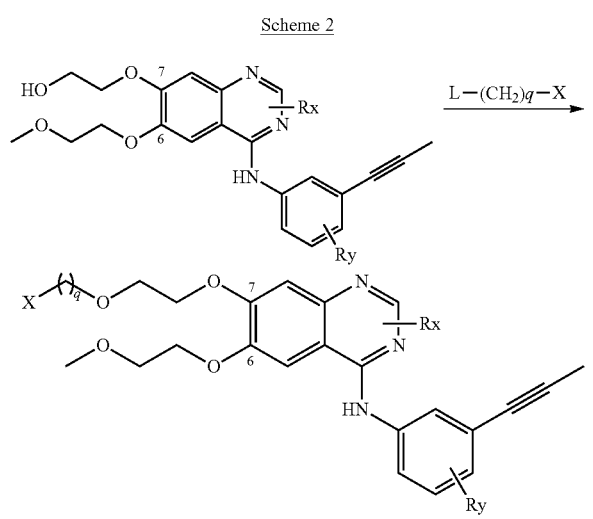

With Rx and Ry being one or more substituents (which can be the same or different) on the quinazoline and aniline rings of erlotinib, respectively, as defined herein for $R_{13}$-$R_{15}$ and $R_{17}$-$R_{20}$, respectively; q being at least 1 (e.g., 1 to 21; and equals n+1); L being a leaving group such as tosyl, mesyl, nosyl, bromide and iodide; and X being a halogen, for example, fluorine.

Such a one step synthesis can be performed using, for example, fluoromethyltosylate [F—CH$_2$—OTs] or fluoroethyltosylate [F—CH$_2$CH$_2$—Ots] or fluoroethyl mesylate, or fluoromethymesylate, or fluoroethylnosylate, fluoromethylnosylate, etc. as reagents.

Exemplary general procedure III involves using as a starting material a compound which features a leaving group at the terminus of the substituent at the 6 or 7 positions and replacing the leaving group with a halogen atoms, as depicted in Scheme 3 below:

Scheme 3

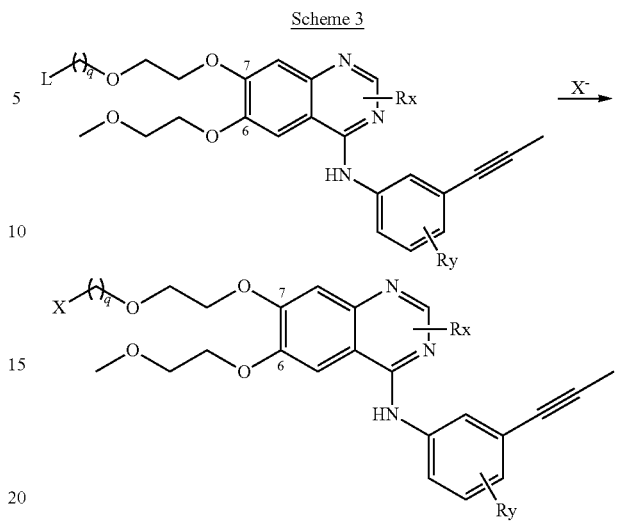

With Rx, Ry, q, L and X as defined hereinabove. Such a synthesis proceeds via a nucleophilic reaction, and any leaving group and halide useful in such reactions can be utilized. Reaction conditions are selected in accordance with the leaving group and halide-containing reagent used.

Similarly, using a starting material having a leaving group at the end of the substituted at position 6, provides the respective 6-haloalkylerlotinib.

Herein throughout, 6-haloalkylerlotinib and 7-haloalkylerloytinib refer to a halogenated erlotinib analog as described herein, in which the terminal methyl of the 2-methoxyethoxy substituent at the 6 or 7 position is replaced by a haloalkyl.

Synthesis, Purification and Characterization of 6-O-fluoroethylerlotinib (6-O-FEE) Standard:

The synthesis of 6-O-FEE was carried out using standard organic chemistry techniques, according to Scheme 1 above. Briefly, 6-O-desmethylerlotinib (15 mg) was dissolved in 3 mL of dry DMF containing 5-7 mg of NaH (5 minutes at room temperature). Fluoroethyltosylate (ABX, Radeberg, Germany, 1.3 equivalents, 51 mmol) was then added, and the reaction was heated to 80° C. for one hour. The reaction was thereafter cooled in an ice bath, and ethanol (2 mL) and crushed ice were added. The reaction was then filtered, concentrated, and the product was purified using preparative C18 HPLC column with a mixture of 63:37 H$_2$O:MeCN including 0.2% TFA as eluent, yielding the final product (23 mg, 32.3%).

The purity of the final product was higher than 99.3%, as determined by analytical HPLC, and the structure was confirmed by $^1$H-NMR, $^{19}$F-NMR and HRMS.

7-O-fluoroethylerlotinib (7-O-FEE), 6-O-fluoromethylerlotinib (6-O-FME), and 7-O-fluoromethylerlotinib (7-O-FME) are similarly prepared, using the respective reagents.

The structures of 6-O-FEE, 6-O-FME, 7-O-FEE and 7-O-FME are presented in FIG. 1.

Radiosynthesis of Radiolabeled 6/7-haloalkylerlotinib—General Procedures:

Based on the above synthetic pathways, general radiosynthesis strategies have been designed for generating radiolabeled-haloalkyl erlotinib compounds.

In an exemplary general procedure, the radiosynthesis is generally a two-step reaction, wherein a radiolabeled haloalkyl reactive compound (e.g., a haloalkyl bearing a reactive leaving group, as defined herein) is prepared, and then reacted with a 6/7-O-desmethyl erlotinib (or a corresponding erlotinib derivative), as depicted in Schemes 4 and 5 below.

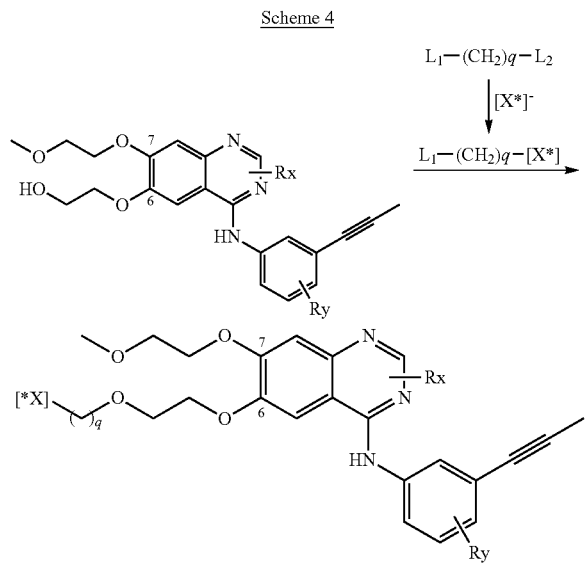

Scheme 4

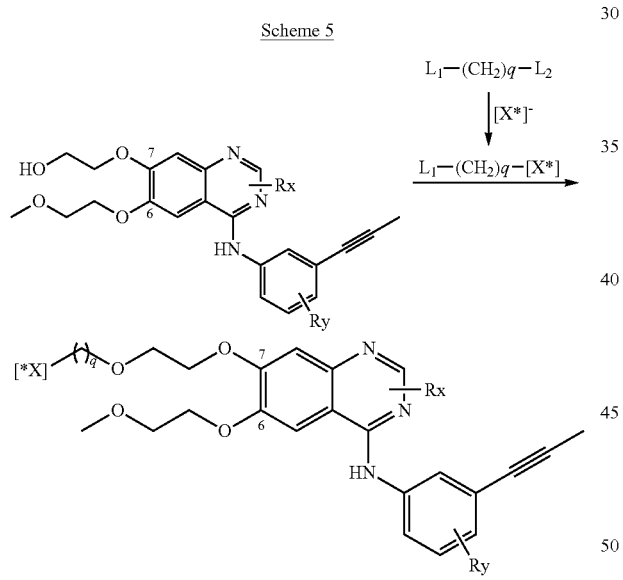

Scheme 5

With Rx and Ry being one or more substituents (which can be the same or different) on the quinazoline and aniline rings of erlotinib, respectively, as defined herein for $R_{13}$-$R_{15}$ and $R_{17}$-$R_{20}$, respectively; q being at least 1 (e.g., 1 to 21; and equals n+1); $L_1$ and $L_2$ being each independently a leaving group as described herein; and X* being a radioactive halogen, for example, fluorine-18.

In another exemplary general procedure, the radiosynthesis is generally a one-step reaction, wherein a reactive erlotinib analog featuring an alkyl terminated by a reactive leaving group is prepared, for example, by reacting a desmethyl derivative of erlotinib (or a derivative thereof), for example 6-desmethylerlotinib (6-O-desmethyl erlotinib) or 7-desmethylerlotinib (7-O-desmethyl erlotinib), with a bifunctional alkyl that features two leaving groups, at different termini thereof, as depicted in Schemes 6 and 7 below. The bifunctional alkyl can be, for example, 1,n-dibromoalkyl, 1,n-diiodoalkyl, 1,n-ditosylalkyl, 1,n-dimesylalkyl, 1,n-dinosylalkyl, such as, but not limited to, 1,2-dibromoethane/methane, 1,2-Dimesylethane/methane, 1,2-Ditosylethane/methane and 1,2-Dinosylethane/methane.

The reactive erlotinib (or a derivative thereof) is thereafter reacted with a radioactive halide, which displaces the leaving group to provide the end radiolabeled product.

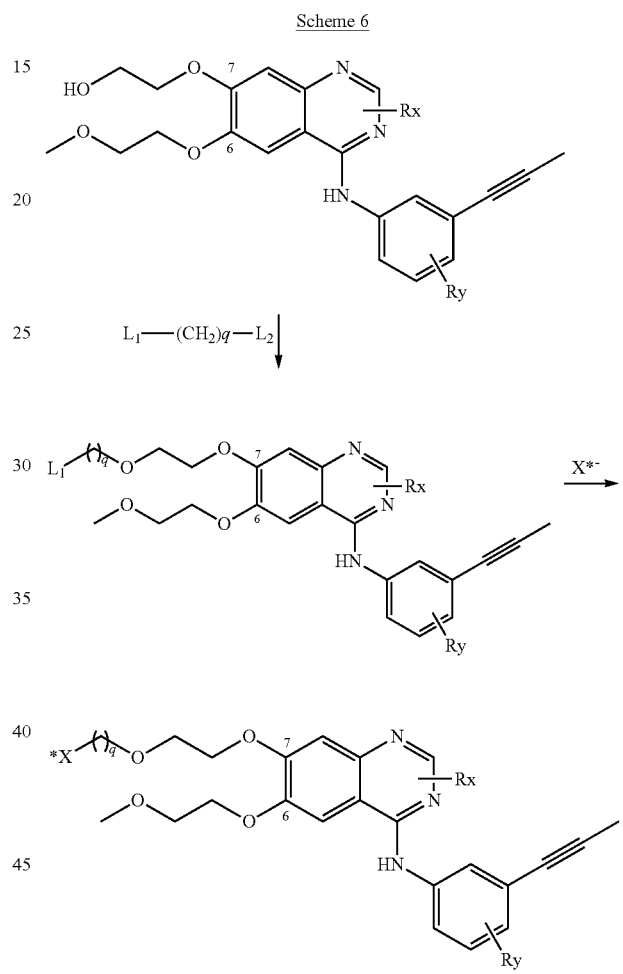

Scheme 6

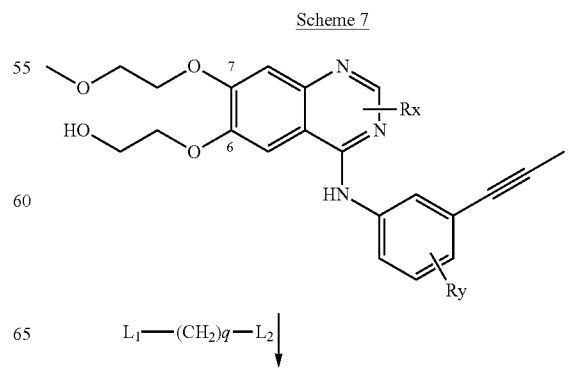

Scheme 7

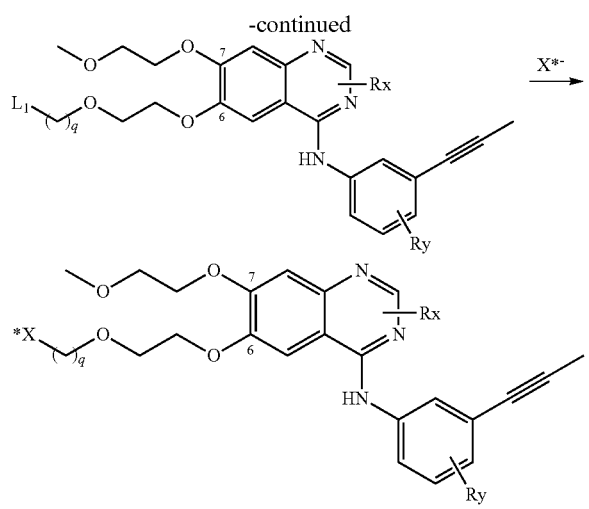

With Rx and Ry being one or more substituents (which can be the same or different) on the quinazoline and aniline rings of erlotinib, respectively, as defined herein for $R_{13}$-$R_{15}$ and $R_{17}$-$R_{20}$, respectively; $L_1$ and $L_2$ being each independently a leaving group as described herein; and $X^{*-}$ being a radioactive halide, for example, fluoride-18.

The reaction conditions can be determined by the selected leaving groups.

Radiosyntheses of [$^{18}$F]6-fluoroethylerlotinib ([$^{18}$F]6-O-FEE):

[$^{18}$F]fluoromethyltosylate is obtained from methylene bis-tosylate, during the production of [$^{18}$F]fluoromethylcholine, as described by Rodnick et al. *Appl Radiat Isot* 2013, 78:26-32. [$^{18}$F]fluoroethyltosylate is similarly prepared from ethylene 1,2-bis(tosylate). The radiosyntheses are depicted in Scheme 8 below.

In brief, a solution of ethylene 1,2-(bis) tosylate (11-13 mg) dissolved in anhydrous MeCN (750 mL) was added to the dried [$^{18}$F]fluoride. The reaction is heated to 120° C. while stirring for 10 minutes, and the reaction mixture was thereafter cooled to 50° C. The $^{18}$F-fluoroethyltosylate was then further diluted with 1 mL MeCN and transferred to a second reactor that was pre-stirred and heated under argon stream for 5 minutes with 9-11 mg of desmethylerlotinib dissolved in 0.6 mL of DMF and 6-8 mg of NaH. The reaction mixture was then heated to 90° C. while stirring for 25 minutes, and was thereafter cooled to 60° C., partially evaporated, filtered, diluted with 1.5 mL of acetate buffer (0.1 M, pH 3.8) and MeCN (6:4, respectively), and separated on a semi-preparative C18 column (5 μm, 10 mm×250 mm, Luna, phenomenex, Torrance, Calif., USA), equipped with a detector operated at 254 nm, using the same acetate buffer: MeCN as eluent, at a flow rate of 4 mL/minute. The final product (retention time at 14 minutes) was collected in a round bottom flask containing 24 mL of HPLC water. The solution was then loaded on C18-Plus Sep-Pak (Waters Corporation, Milford, Mass., USA, pre-activated with 5 mL ethanol and 10 mL of HPLC water) and washed with additional 4 mL of HPLC water. The product was thereafter eluted using 1.8 mL ethanol and further diluted using 18.2 mL of isotonic saline.

The final formulation (20 mL) typically contains 10% or less ethanol, and is optionally submitted for quality control testing.

The overall synthesis time was 110 minutes, including purification and formulation from the end-of bombardment.

An average activity of 12.1+/−4.1 GBq (n=6) decay corrected to the end of bombardment (DC EOB) was obtained with 7.1% average of radiochemical yield and specific activity of 109.5+/−40.3 GBq DC to EOB.

The radiochemical purity was determined using analytical HPLC equipped with C18 analytical Luna column (5 μm, 4.6 mm>250 mm, Luna, phenomenex, Torrance, Calif., USA), with a variable wavelength UV detector operated at λ=254 nm, and a radioactivity detector with NaI crystals, and was routinely greater than 98%. Identification of [$^{18}$F] 6-O-FEE was confirmed by a co-injection of unlabeled 6-O-FEE, having retention times of 9.9 minutes and 9.3 minutes, respectively. To confirm the absence of kryptofix 2.2.2 in the final product, a color spot test was performed using a coated silica gel thin-layer chromatographic strip, saturated with an iodoplatinate reagent. Standard solutions of 0, 0.025, 0.05 and 0.01 mg/mL of kryptofix 2.2.2 standard were used as reference standards. Solvent residues were analyzed by GC, using a 1 μL injection of the final product, and compared to a standard solution containing 0.04% acetonitrile and 0.5% acetone. Standard area counts and corresponding retention times for acetonitrile and acetone were 23,172 area counts at 6.4 minutes and 275,328 area counts at 8.9 minutes, respectively. The solution was inspected for its clearness and transparency and was colorless or, in some cases, light yellow. The solution pH was confirmed as 5-5.5 by pH indicator strips (pH 4-7, Merck, Darmstadt, Germany). [$^{18}$F]6-O-FEE remained stable in solution for over four hours, as confirmed by radio-TLC (using 10% methanol in dichloromethane as eluent) and HPLC.

Scheme 8

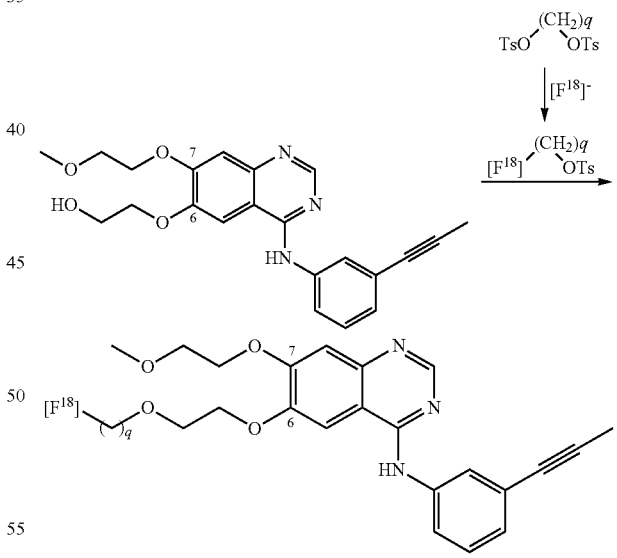

Example 2

In Vitro Assays

Materials:

NCI-H1975 and HCC827 were obtained from the ATCC. QG56 cells were obtained from Prof. Alexander Levitzki's lab, The Silberman Institute of Life Sciences, the Hebrew University, Jerusalem. The NCI-H3255 human NSCLC cell line was obtained from the National Cancer Institute—Division of Cancer Treatment and Diagnosis (NCI-DCTD) tumor repository, Frederick, Md., USA, and was regularly maintained in ACL-4 medium, containing insulin (0.02 mg/ml), transferrin (0.01 mg/ml), sodium selenite (25 nM), hydrocortisone (50 nM), EGF (1 ng/ml), ethanolamine (0.01 mM), O-phosphorylethanolamine (0.01 mM), triiodothyronine (100 pM), BSA (0.2% (w/v)), HEPES (10 mM), sodium pyruvate (0.5 mM) and L-glutamine (2 mM) in RMPI-1640 medium (Invitrogen™, Life Technologies, Mass., USA). QG56 were maintained in RMPI-1640 medium (Invitrogen™). HCC827 and NCI-H1975 cells were maintained in RMPI-1640 (#30-2001, ATCC), at 37° C. in a humidified atmosphere of 95% air and 5% $CO_2$. All media were supplemented with fetal bovine serum (FBS, (10%)) and antibiotics (penicillin $10^4$ units/L, streptomycin 10 mg/L) (BI, Israel).

Cell Growth Inhibition:

Four human NSCLC cell lines were selected: QG56, HCC827, NCI-H3255 and NCI-H1975. These cell lines harbor the prevailing EGFR variants identified in NSCLC patients, including the wild-type receptor (QG56 cells) and the two most common activating mutations in the TK domain of the receptor: an exon 19 deletion (ΔE746-A750) (HCC827 cells) and the L858R point mutation in exon 21 (NCI-H3255). NCI-H1975 cells were also selected, since on top of the activating L858R point mutation, these cells harbor the secondary T790M mutation in exon 20, which confers resistance to TKI-therapy. This panel of cell lines therefore represents the principal spectrum of EGFR variants detected in NSCLC patients.

The sensitivity of the four human NSCLC cell lines to the anti-proliferative effect of 6-O-FEE was determined in vitro, and compared to that of erlotinib.

Specifically, cells were incubated with increasing concentrations of the tested compounds (0-100 μM in 0.0 5% DMSO, 0.1% ethanol) for 72 hours, and their viability at the end of treatment was determined using the methylene blue assay.

The median inhibitory concentration (IC50) of the tested compound for cell growth of each cell line was then calculated using GraphPad Prism 5.0 software. The obtained data is presented in Table 1. Results are presented as mean±SD.

As shown in Table 1, erlotinib and 6-O-FEE exhibit comparable potency and selectivity towards cells lines that harbor an EGFR with either activating mutations. Both erlotinib and 6-O-FEE had $IC_{50}$ values 2-3 orders of magnitude higher with respect to the TKI-resistant (NCI-H1975) and the TKI-insensitive (QG56) cell lines, compared to the TKI-sensitive (NCI-H3255 and HCC827) cells.

TABLE 1

| Cell line | Type of EGFR mutation | $IC_{50}$ of erlotinib [μM] | $IC_{50}$ of 6-O-FEE [μM] |
|---|---|---|---|
| NCI-H1975 | Double (L858R + T790M) | 3.1 ± 1 (n = 2) | 3.6 ± 1 (n = 3) |
| HCC827 | Activating (delE746-A750) | 0.001 ± 0.00 (n = 3) | 0.007 ± 0.01 (n = 3) |
| NCI-H3255 | Activating (L858R point mutation) | 0.046 ± 0.03 (n = 3) | 0.033 ± 0.04 (n = 3) |
| QG56 | None (wt EGFR) | 12.7 ± 6 (n = 4) | 14.4 ± 5 (n = 3) |

Example 3

Pet Studies

PET/CT Scans of Tumor-Bearing Mice:

Dynamic (1 hour) PET scans are performed using Inveon™ MM PET-CT small animal-dedicated scanner (Siemens Medical Solutions, USA). PET acquisitions of NSCLC tumor-bearing mice are carried out following intravenous (i.v.) administration of $^{18}$F-labeled erlotinib analogs as described herein. Using image analysis tools, volume of interests (VOIs) are drawn for selected organs based on the PET and CT images, and the kinetics of radioactivity distribution in vivo (time-activity curves, (TACs)) is determined for these organs, and primarily for the NSCLC xenografts. The standardized uptake values (SUVs) of each radiolabeled compound in tumors are calculated and compared between the different tumors.

In a preliminary PET/CT study, three mice (two bearing HCC827 (erlotinib-sensitive) tumors and one with an NCI-H1975 (erlotinib-resistant tumor) were scanned for 60 minutes following i.v. injection of [$^{18}$F]6-FEE (6.26±4.4 Mbq). The obtained data is presented in FIG. 2 and show that the $^{18}$F-labeled erlotinib analog exhibits a 2.5-3-fold higher uptake in HCC827 tumor compared to NCI-H1975 tumor, thus indicating that this analog can differentiate TKI-sensitive from TKI-resistant tumors.

FIG. 3 presents PET/CT slice images of mice bearing HCC827 tumor (left and middle panels) and a mouse bearing NCI-H1975 tumor (right panel), at 30-60 minutes following i.v. injection of [$^{18}$F]6-FEE (top) and 40-60 minutes after injection of [$^{18}$F]FDG (bottom). Mice were scanned for 60 minutes following injection of [$^{18}$F]6-FEE, maintained at the same position for injection of [$^{18}$F]FDG, and scanned again 40 minutes later. Green arrows point at the location of tumors.

The obtained images further support the ability of the $^{18}$F-labeled erlotinib analog to differentiate TKI-sensitive from TKI-resistant tumors. The imaging data obtained upon [$^{18}$F]FDG injection confirmed existing of tumors.

In additional PET/CT studies, five QG56 (erlotinib-insensitive) and five HCC827 (erlotinib-sensitive) tumor-bearing mice were scanned for 60 minutes following i.v. injection of [$^{18}$F]6-O-FEE (7.14±0.7 Mbq). The obtained data is presented in FIG. 4 and show that at 60 minutes after injection, [$^{18}$F]6-O-FEE exhibits a 2.5-fold higher uptake in HCC827 tumors compared to QG56 tumors (SUV=0.70 vs. 0.28, p=0.0072), thus indicating that this analog can differentiate TKI-sensitive from TKI-insensitive tumors. When erlotinib was administered in excess (6.1±0.3 mg/kg) 10 minutes prior to the injection of [$^{18}$F]6-O-FEE into HCC827 tumor-bearing mice, the tumor SUV was reduced by about 40% (0.704 vs. 0.414, p=0.018), indicating specific binding of the radiolabeled analog to the EGFR.

FIGS. 5A-C presents PET/CT slice images of a mouse bearing an HCC827 tumor without (FIG. 5A) and following (FIG. 5B) pre-administration of non-labeled erlotinib in excess, and a mouse bearing a QG56 tumor (FIG. 5C), at 30-60 minutes following i.v. injection of [$^{18}$F]6-FEE. Green arrows point at the location of tumors.

As can be seen, the data obtained in the studies shown in FIGS. 4 and 5A-C provided statistically significant differences.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A radiolabeled compound represented by general Formula Ia or Ib:

Formula Ia

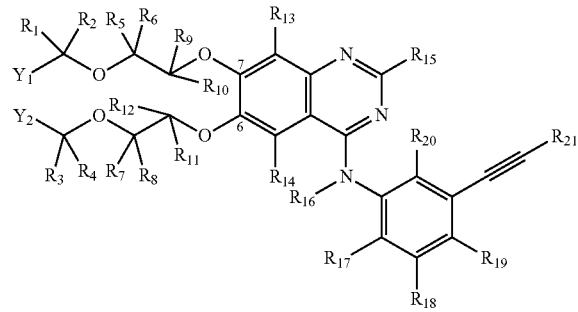

Formula Ib

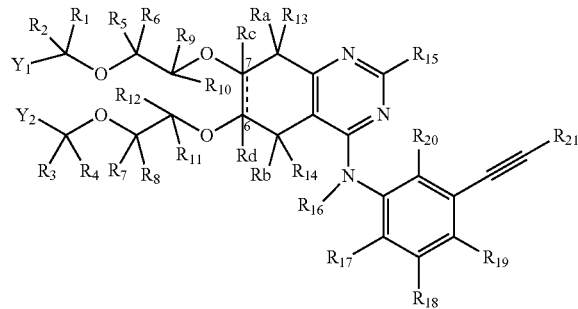

wherein:
the dashed line in Formula Ib denotes an optional unsaturated bond;
$R_1$-$R_{21}$, Ra and Rb are each hydrogen;
Rc and Rd are each absent, in case the dashed line denotes an unsaturated bond, or are each hydrogen; and
$Y_1$ and $Y_2$ are each independently selected from hydrogen, alkyl, cycloalkyl, alkoxy, hydroxyl, a substituted or unsubstituted, saturated or unsaturated hydrocarbon chain of 1 to 20 carbon atoms, optionally interrupted by one or more heteroatoms, a radioactive halogen, and Q, wherein Q is a chemical moiety comprising a radioactive halogen,
provided that at least one of $Y_1$ and $Y_2$ is said radioactive halogen or said Q.

2. The radiolabeled compound of claim 1, wherein at least one of $Y_1$ and $Y_2$ is said Q.

3. The radiolabeled compound of claim 2, wherein Q is a saturated or unsaturated hydrocarbon chain of 2 to 20 carbon atoms, optionally interrupted by one or more heteroatoms, substituted by or terminating with said radioactive halogen.

4. The radiolabeled compound of claim 2, wherein Q is an alkylene chain or is or comprises an alkylene glycol or a derivative thereof, each being substituted by or terminating with said radioactive halogen.

5. The radiolabeled compound of claim 2, wherein Q is (CR'R")nX,
wherein R' and R" are each hydrogen;
n is an integer of from 1 to 20; and
X is said radioactive halogen.

6. The radiolabeled compound of claim 5, wherein n is 2.

7. The radiolabeled compound of claim 1, wherein at least one of $Y_1$ and $Y_2$ is said radioactive halogen.

8. The radiolabeled compound of claim 1, represented by Formula Ia.

9. The radiolabeled compound of claim 1, wherein said radioactive halogen is fluorine-18.

10. A pharmaceutical composition comprising as an active ingredient the radiolabeled compound of claim 1 and a pharmaceutical acceptable carrier.

11. A method of radioimaging, the method comprising administering to a patient in need thereof the radiolabeled compound of claim 1 and employing a nuclear imaging technique to thereby determine a level and/or distribution of the compound in the patient's body or a portion thereof.

12. The method of claim 11, wherein being for monitoring or determining a level and/or distribution and/or mutational status of an epidermal growth factor receptor (EGFR) within the body of the patient.

13. The method of claim 12, being for determining if the patient has a disease or disorder associated with deregulated expression and/or activity of EGFR.

14. The method of claim 13, wherein said disease or disorder is a proliferative disease or disorder.

15. The method of claim 12, being for monitoring or determining a presence or absence of an activating mutation in the tyrosine kinase domain of an EGFR gene which confers sensitivity to an inhibitor of EGFR-TK; and/or
for determining if the patient has a disease or disorder treatable by an inhibitor of EGFR-TK; and/or
for determining if the patient is responsive to a treatment with an inhibitor of EGFR-TK inhibitor.

16. The method of claim 15, wherein said inhibitor of EGFR-TK is erlotinib.

17. The method of claim 11, wherein said patient is diagnosed as having, or as suspected of having, a disease or disorder associated with deregulated expression and/or activity of EGFR.

18. The method of claim 17, wherein said patient is diagnosed as having, or as suspected of having, a proliferative disease or disorder.

19. The method of claim 18, wherein said proliferative disease or disorder is selected from the group consisting of non-small cell lung cancer (NSCLC), pancreatic cancer, head and neck squamous cell carcinoma (HNSCC), brain cancer, breast cancer, esophageal cancer, gastric cancer, renal cancer, cervical cancer, ovarian cancer, hepatocellular cancer, malignant glioma, prostate cancer, colorectal cancer (CRC), bladder cancer, gynecological cancer, thyroid cancer and lymphoma.

20. A method of treating a patient diagnosed with a disease or disorder associated with deregulated expression and/or activity of EGFR, the method comprising:
administering the radiolabeled compound of claim 1 to the patient;

determining a level and/or distribution of the radiolabeled compound in the patient's body or a portion thereof by employing a nuclear imaging technique, said level and/or distribution being indicative of the patient's responsiveness to a treatment with an inhibitor of EGFR-TK; and based on said determining, administering to the patient an inhibitor of EGFR-TK or an agent for regulating the expression and/or activity of EGFR other than an inhibitor of EGFR-TK.

21. The method of claim 20, wherein following said determining the patient is administered with said inhibitor of EGFR-TK for a first time period, the method further comprising, following said first time period, determining an emergence of a resistance to said inhibitor of EGFR-TK, said determining comprising:

administering the radiolabeled compound or the composition to the patient;

determining a level and/or distribution of the radiolabeled compound in the patient's body or the portion thereof by employing said nuclear imaging technique, said level and/or distribution being indicative of the patient's responsiveness to a treatment of an inhibitor of EGFR-TK; and based on said determining, administering to the patient said inhibitor of EGFR-TK for a second time period or administering to the patient said another agent for regulating said expression and/or activity of EGFR for said second time period.

22. The method of claim 11, wherein said technique is positron emission tomography.

23. The method of claim 20, wherein said technique is positron emission tomography.

24. A method of radiotherapy, the method comprising administering to a subject in need thereof a therapeutically effective amount of the radiolabeled compound of claim 1.

25. The method of claim 24, wherein said patient is diagnosed with deregulated expression and/or activity of EGFR.

26. The method of claim 24, wherein said patient is diagnosed as having a disease or disorder that is treatable by an inhibitor of EGFR-TK.

27. A process of preparing the radiolabeled compound of claim 1, the process comprising reacting a compound represented by Formula IIa or IIb:

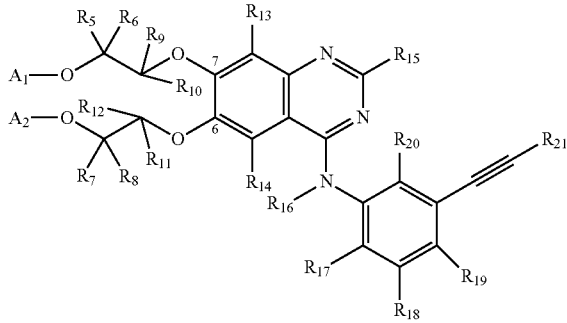

Formula IIa

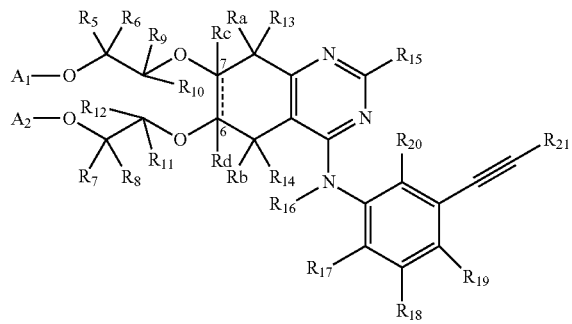

Formula IIb wherein:

$A_1$ is $-CR_1R_2B_1$, $-CR_1R_2Q_1W_1$, or forms with the oxygen to which it is attached $W_1$; and $A2$ is $-CR_3R_4B_2$, $-CR_3R_4Q_2W_2$, or forms with the oxygen to which it attached $W_1$;

$B_1$ and $B_2$ are each independently as defined for $R_1$-$R_{21}$;

$Q_1$ and $Q_2$ are each independently as defined for Q or is absent; and $W_1$ and $W_2$ are each independently a reactive group, provided that at least one of $A_1$ and $A2$ forms with the oxygen to which it is attached, or comprises, said reactive group, with a compound represented by Formula III(1) and/or III(2):

$$L_A\text{-}(CR_1R_2)m(Q)k\text{-}Z \qquad \text{Formula III(1)}$$

$$L_A\text{-}(CR_3R_4)m(Q)k\text{-}Z \qquad \text{Formula III(2)}$$

wherein:

$L_A$ is a leaving group;

Z is said radioactive halogen; and m is 0 or 1; and k is 0 or 1, whereas:

said compound of Formula III(1) is reacted with a compound represented by Formula IIa or IIb in which $A_1$ forms, or comprises, said $W_1$, and a compound represented by Formula III(2) is reacted with a compound represented by Formula IIa or IIb in which $A_2$ forms a part of, or comprises, said $W_2$;

when $A_1$ forms with the oxygen atom to which it is attached said $W_1$, m in Formula III(1) is 1;

when $A_2$ forms with the oxygen atom to which it is attached said $W_2$, m in Formula III(2) is 1;

when $A_1$ is $-CR_1R_2Q_1W_1$, m and k in Formula III(1) are each 0; and when $A_2$ is $-CR_3R_4Q_2W_2$, m and k in Formula III(2) are each 0.

* * * * *